US012429429B2

(12) United States Patent
Lin

(10) Patent No.: US 12,429,429 B2
(45) Date of Patent: Sep. 30, 2025

(54) METHOD AND APPARATUS FOR WASTE LIQUID RECYCLING WITH OPTICAL INSPECTION

(71) Applicant: Hsiu-An Lin, Kaohsiung (TW)

(72) Inventor: Hsiu-An Lin, Kaohsiung (TW)

( * ) Notice: Subject to any disclaimer, the term of this patent is extended or adjusted under 35 U.S.C. 154(b) by 118 days.

(21) Appl. No.: 18/537,434

(22) Filed: Dec. 12, 2023

(65) Prior Publication Data

US 2024/0210326 A1 Jun. 27, 2024

(30) Foreign Application Priority Data

Dec. 23, 2022 (EP) ..................... 22216299

(51) Int. Cl.
*G01N 21/85* (2006.01)
*G01N 15/0227* (2024.01)
*G01N 15/1433* (2024.01)

(52) U.S. Cl.
CPC ......... *G01N 21/85* (2013.01); *G01N 15/0227* (2013.01); *G01N 15/1433* (2024.01)

(58) Field of Classification Search
CPC .............. G01N 21/85; G01N 15/0227; G01N 15/1433; G01N 33/1833; G01N 33/26; G01N 21/251; G01J 3/462; G01J 3/28; G01J 3/50
USPC ........................................ 356/402
See application file for complete search history.

(56) References Cited

U.S. PATENT DOCUMENTS

2010/0312601 A1 12/2010 Lin

FOREIGN PATENT DOCUMENTS

| CN | 110320158 A | * | 10/2019 | ............ G01N 21/01 |
| CN | 111103289 A | * | 5/2020 | ............ G01N 21/85 |
| CN | 111474309 A | | 7/2020 | |
| EP | 3647766 A1 | | 5/2020 | |
| EP | 4001892 A1 | | 5/2022 | |
| KR | 102378076 B1 | | 3/2022 | |
| TW | 201044209 A1 | | 12/2010 | |
| TW | 201120792 A | | 6/2011 | |
| TW | 201122458 A | | 7/2011 | |

(Continued)

OTHER PUBLICATIONS

European Patent Office "European patent application No. 22216299.2 Extended European Search Report" issued on May 4, 2023.

(Continued)

*Primary Examiner* — Md M Rahman
(74) *Attorney, Agent, or Firm* — WPAT, PC

(57) ABSTRACT

A method and an apparatus for waste liquid recycling with optical inspection are provided. The method includes: establishing a plurality of statistical criteria; capturing an image of a waste liquid in a transparent pipeline; performing image processing on the image of the waste liquid to obtain a plurality of characteristic data about a color characteristic; performing statistical calculation processing on the plurality of characteristic data to obtain a plurality of statistical characteristic values; and selecting at least one statistical criterion from the plurality of statistical criteria to compare with the statistical characteristic values so as to determine the quality of the waste liquid.

15 Claims, 24 Drawing Sheets
(20 of 24 Drawing Sheet(s) Filed in Color)

(56) References Cited

FOREIGN PATENT DOCUMENTS

TW           201122458 A1     7/2011
TW           202016534 A      5/2020

OTHER PUBLICATIONS

European Patent Office "European patent application No. 23215744. 6Extended European Search Report" issued on May 22, 2023.
Taiwan Intellectual Property Office "Taiwan patent applications No. 112145440 Office Action and search report" issued on Sep. 24, 2024.
Taiwan Intellectual Property Office "Taiwan patent applications No. 112145441 Office Action and search report" issue on Sep. 24, 2024.
China Patent Office International Search Authority "International search report" issued on Feb. 26, 2024.

\* cited by examiner

IMG1

| | mean | r_median | r_range | r_quantile | r_std | r_skewness |
|---|---|---|---|---|---|---|
| IMG1 | 162 | 163 | 132 | 28 | 21.87 | 26.34 |
| IMG2 | 149 | 150 | 132 | 25 | 21 | 24.95 |
| | 153 | 155 | 159 | 24 | 22.66 | 29.48 |
| | 154 | 158 | 90 | 23 | 19.07 | 22.23 |
| | 156 | 153 | 151 | 31 | 25.62 | 31.22 |
| | 146 | 149 | 99 | 21 | 17.74 | 21.09 |
| | 155 | 151 | 121 | 19 | 19.39 | 24.37 |
| | 149 | 151 | 130 | 21 | 19.19 | 23.66 |
| | 142 | 138 | 69 | 15 | 13.32 | 15.96 |
| | 160 | 152 | 138 | 35 | 30.95 | 37.66 |
| | 145 | 145 | 137 | 20 | 20.64 | 27.13 |
| | 151 | 146 | 146 | 39 | 25.69 | 29.61 |
| | 163 | 163 | 115 | 20 | 17.27 | 21.05 |
| | 148 | 150 | 129 | 26 | 21.14 | 24.82 |
| | 151 | 151 | 97 | 37 | 21.47 | 23.66 |
| | 146 | 141 | 128 | 26 | 23.68 | 30.04 |
| | 158 | 151 | 136 | 26 | 28.49 | 36.04 |
| IMG n | 156 | 154 | 132 | 14 | 17.11 | 23.66 |

FIG. 12

METHOD AND APPARATUS FOR WASTE LIQUID RECYCLING WITH OPTICAL INSPECTION

BACKGROUND

1. Field of the Disclosure

The present disclosure relates to a technology for recycling and inspecting waste liquid, particularly to a method and an apparatus for waste liquid recycling with optical inspection, which determines the quality of waste liquid by color characteristics.

2. Description of the Related Art

Waste oil, whether mineral oil or animal and vegetable oil, can be used as a fuel or a recycled raw material for an engine, a combustor or a boiler as long as it is processed and refined, so it is a typical "green energy." The development of the green energy can promote the sustainable development of economy, save energy, reduce carbon emissions and reduce environmental pressure, and can also make an important contribution to urban air pollution control and waste liquid recycling.

However, in recent years, it is often found that unscrupulous operators prepare the waste liquid into edible oil for sale to gain huge profits. It is often revealed in TV and media that waste lubricating oil or waste solvents are illegally dumped to pollute hillsides, rivers, soil and even oceans, it is hard for environmental protection units cannot master the source and disposing direction of the waste liquid (such as waste edible oil, waste lubricating oil and waste solvents), nor can they effectively prevent the waste liquid from entering underground factories or being illegally dumped. In addition, with the public opinions and news media reports, it urgently needs a set of efficient and simple management systems and methods to manage the source and the disposing direction of the waste liquid to achieve dual standards of production source tracing and decontamination history, which is the benefit of all the people.

In the process of waste liquid recycling, confirming the quality of the waste liquid is a very important link. If the waste liquid is determined to be qualified and recoverable, it is needed to formulate a recycling specification to confirm the quality of the recycled waste liquid, and then the price of the waste liquid can be accurately calculated.

However, the water content, acid value, residues and other factors of the waste liquid will affect the quality of the waste liquid, and these influencing factors may be different due to different types of users. Therefore, the recycling specification of single type cannot meet the requirements of different types of users, it is needed various types of recycling specifications to determine the recycling quality of the waste liquid.

Therefore, it is necessary to provide a method and an apparatus for waste liquid recycling to solve the above problems.

SUMMARY

In some embodiments, a method for waste liquid recycling with optical inspection includes: establishing a plurality of statistical criteria; capturing an image of a waste liquid in a transparent pipeline; performing image processing on the image of the waste liquid to obtain a plurality of characteristic data about a color characteristic; performing statistical calculation processing on the plurality of characteristic data to obtain a plurality of statistical characteristic values; and selecting at least one statistical criterion from the plurality of statistical criteria to compare with the statistical characteristic values so as to determine the quality of the waste liquid.

In some embodiments, an apparatus for waste liquid recycling with optical inspection includes a transparent pipeline, an image capturing device and an operation processing device. The transparent pipeline is configured to allow a waste liquid to pass through. The image capturing device is arranged on one side of the transparent pipeline and configured to capture an image of the waste liquid in the transparent pipeline. The operation processing device is electrically connected to the image capturing device. A plurality of statistical criteria are stored in the operation processing device. The operation processing device is configured to perform image processing on the image of the waste liquid to obtain a plurality of characteristic data about a color characteristic, perform statistical calculation processing on the plurality of characteristic data to obtain a plurality of statistical characteristic values, and select at least one statistical criterion from the plurality of statistical criteria to compare with the statistical characteristic values so as to determine the quality of the waste liquid.

In some embodiments, a method for waste liquid recycling with optical inspection includes: calculating a plurality of statistical characteristic values about color characteristics of each image according to color characteristic data containing a plurality of waste liquid images, and establishing a big data database; and obtaining at least one statistical criterion for classifying the quality of the waste liquid through an artificial intelligence model by taking the plurality of statistical characteristic values in the big database as a training and learning basis. The at least one statistical criterion can be used in different areas and different countries, and the recycling specification is changed along with the environment, so the quality of the waste liquid can be accurately and efficiently determined even if the apparatus is placed in different areas and countries.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Aspects of some embodiments of the present disclosure are readily understood from the following detailed description when read with the accompanying figures. It is noted that various structures may not be drawn to scale, and dimensions of the various structures may be arbitrarily increased or reduced for clarity of discussion.

FIG. 12 is an RGB characteristic value list corresponding to each image.

DETAILED DESCRIPTION

Figure 1:
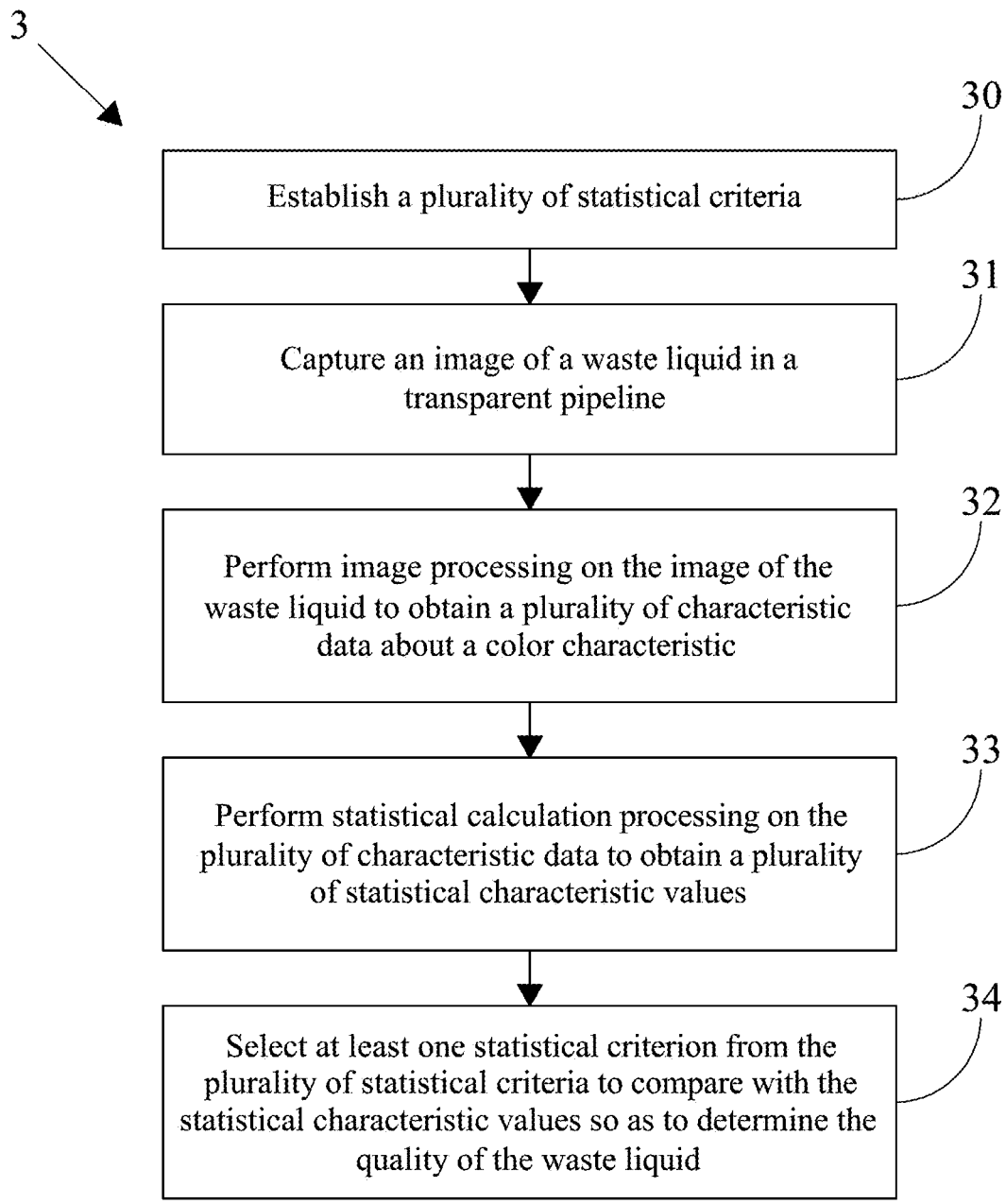
FIG. 1 is a flow schematic diagram of one embodiment of a method for waste liquid recycling with optical inspection of the present disclosure.

Common reference numerals are used throughout the drawings and the detailed description to indicate the same or similar components. Embodiments of the present disclosure will be readily understood from the following detailed description taken in conjunction with the accompanying drawings.

Figure 2:
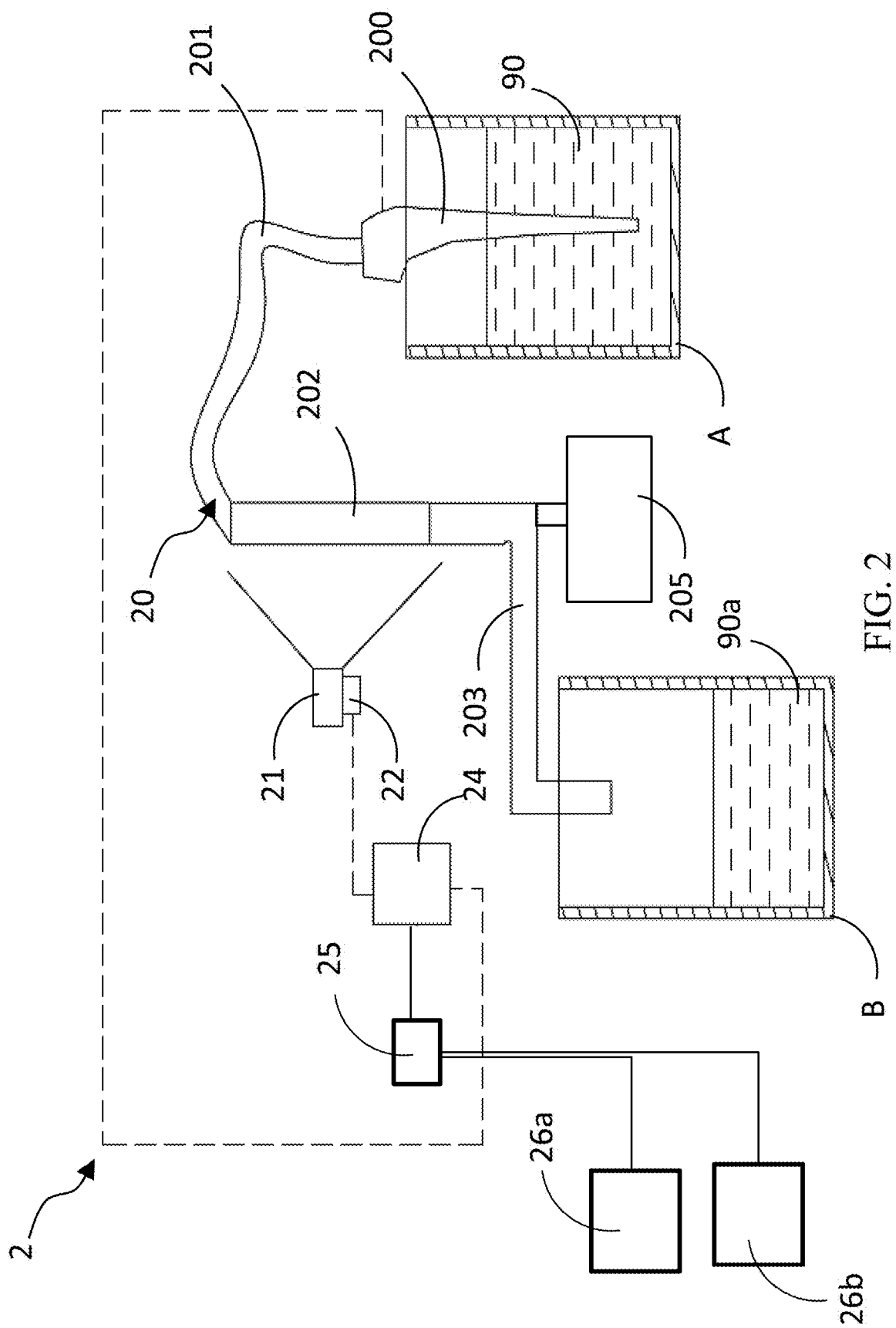
FIG. 2 is an architecture schematic diagram of one embodiment of an apparatus for waste liquid recycling of the present disclosure.

FIG. 1 is the flow schematic diagram of one embodiment of a method 3 for waste liquid recycling with optical inspection of the present disclosure. In some embodiments, the method 3 can include a step 30 of providing an apparatus for waste liquid recycling and establishing a plurality of statistical criteria. FIG. 2 is the architecture schematic diagram of one embodiment of an apparatus 2 for waste liquid recycling of the present disclosure. The apparatus 2 for waste liquid recycling includes a draining device 20, an illuminating device 21, an image capturing device 22 and an operation processing device 24.

In some embodiments, waste liquid 90 is accommodated in a container A. The waste liquid 90 can be waste liquid worth recycling, such as waste engine oil, waste edible oil or to-be-discharged waste liquid like waste water. In some embodiments, the waste liquid is illustrated through the waste edible oil. The container A can be a waste oil recycling barrel used by catering workers providing the waste edible oil, or a container used by general people at home, or a frying oil tank of the catering workers, etc., and it has no certain limitation.

In some embodiments, the draining device 20 is provided with a draining nozzle 200, a draining pipeline 201 and a transparent pipeline 202, where the draining nozzle 200 extends into the container A and is used for draining the waste liquid 90 in the container A. The draining pipeline 201 is used for guiding the waste liquid 90 drained from the draining nozzle 200. The transparent pipeline 202 is in communication connection with the draining pipeline 201, so that the waste liquid 90 in the draining pipeline 201 can pass through the transparent pipeline 202, namely the transparent pipeline 202 is configured to allow the waste liquid 90 to pass through. A guide pipeline 203 is connected behind the transparent pipeline 202 and is used for guiding the waste liquid 90a which passes through the guide pipeline 203 and meets the recycling quality standard to a waste liquid accommodating apparatus B. The draining principle of the draining device 20 is well known in the art and can be implemented in multiple manners. In some embodiments, pipeline negative pressure is provided by a negative pressure generating apparatus 205 and is transferred to the draining nozzle 200 through the draining pipeline 201, thereby draining the waste liquid 90 from the container A.

The illuminating device 21 can be arranged on the image capturing device 22 and used for illuminating the transparent pipeline 202. A light source generated by the illuminating device 21 is not limited specifically, and can be broadband light, such as white light or narrow-band light like laser light, or infrared light, a user can determine the light source according to needs, it has no certain limitation. The image capturing device 22 is configured to capture an image of the illuminated transparent pipeline 202 or an image of the waste liquid 90 in the transparent pipeline 202 in the process of draining the waste liquid 90 by the draining device 20 so as to generate at least one image signal. It is to be noted that the image capturing device 22 and the illuminating device 21 can be arranged on the same side or different sides. For example, in some embodiments, the image capturing device and the illuminating device are arranged on the same side. In some embodiments, the image capturing device 22 can also be arranged on the other side of the transparent pipeline 202 relative to the illuminating device 21, so that the image capturing device and the illuminating device are opposite to each other. In addition, it is to be noted that the illuminating device 21 is not an essential element, it depends on the state of ambient light, so the illuminating device is not an essential apparatus.

It is to be noted that the transparent pipeline 202 is made of a light-transmitting material, such as glass or plastic, so when the waste liquid 90 passes through the transparent pipeline, the waste liquid inside the transparent pipeline 202 can present light transmittance under the light source of the illuminating device 21; due to the components of the waste liquid, the light transmittance of the waste liquid can be different, and thus the colors presented by waste liquid images are different. For example, the light transmittance of the waste liquid might be influenced by the proportion of the water content in the waste liquid, so the light transmittance of the waste liquid can be changed along with the change of the proportion of the water content, and the inspection can be immediately carried out in an image observation manner by means of this phenomenon. Namely, the quality can be determined within a short time, such as within one second or shorter. Therefore, the image of the transparent pipeline 202 can be captured by the image capturing device 22 under the condition that the transparent pipeline 202 is illuminated by lamplight, thus the waste liquid image can be generated, and the quality of the waste liquid in the pipeline can be analyzed through the characteristics presented by the waste liquid image.

In some embodiments, the operation processing device 24 can be electrically connected to the image capturing device 22. The operation processing device 24 can be a computer, an industrial computer or a programmable logic controller (PLC) with operation processing capability. The plurality of statistical criteria can be stored in the operation processing device 24. The statistical criteria are statistical values formed by statistical value characteristics about the color characteristics of the waste liquid, such as but not limited to mean, median, range, interquartile range, standard deviation, and skewness. In some embodiments, the statistical criteria can also be referred to as "statistical standard," "statistical benchmark," or "statistical norm."

Figure 3:
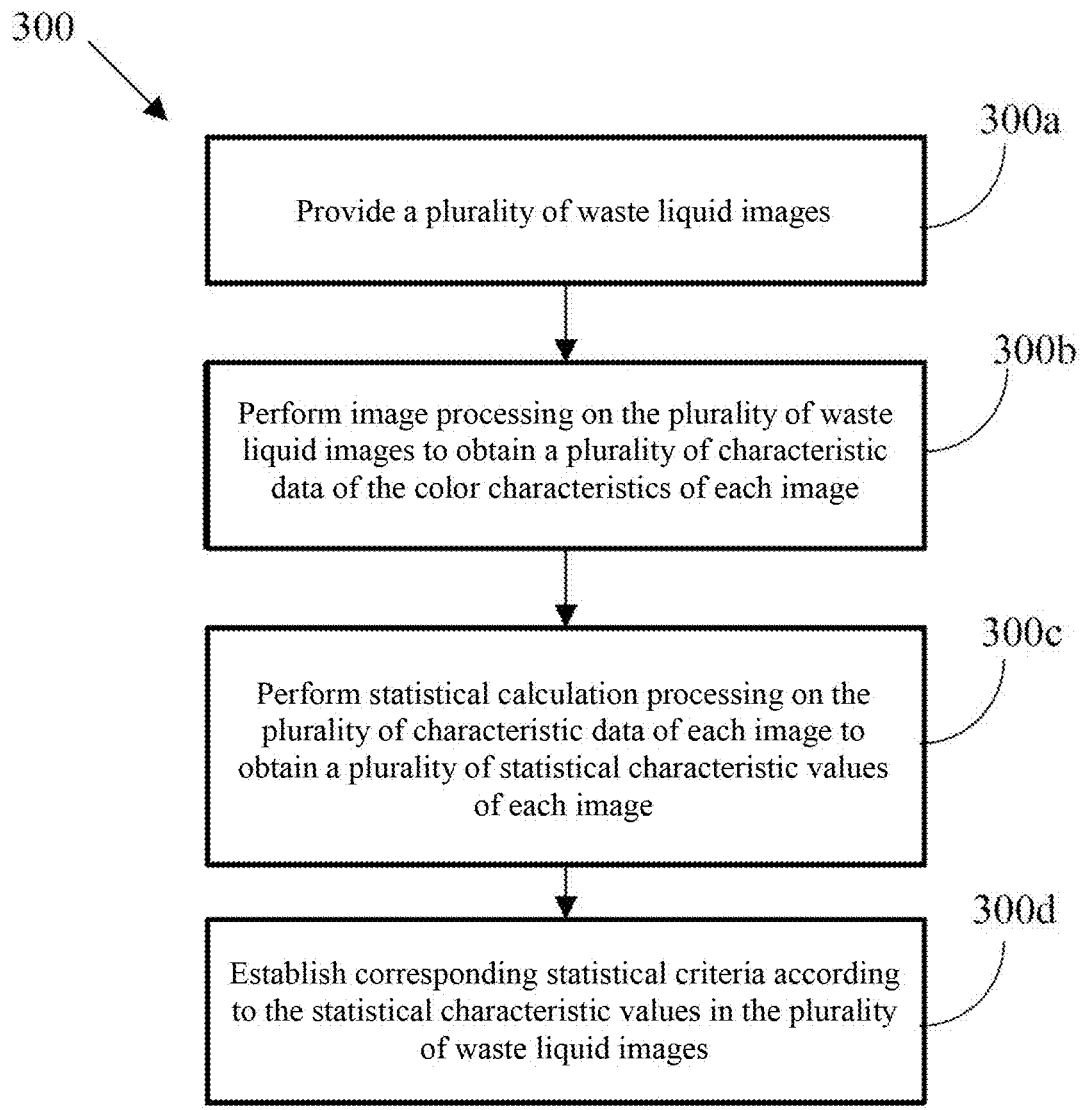
FIG. 3 is a flow schematic diagram of one embodiment of a method for establishing statistical criteria of the present disclosure.
Figure 4A:
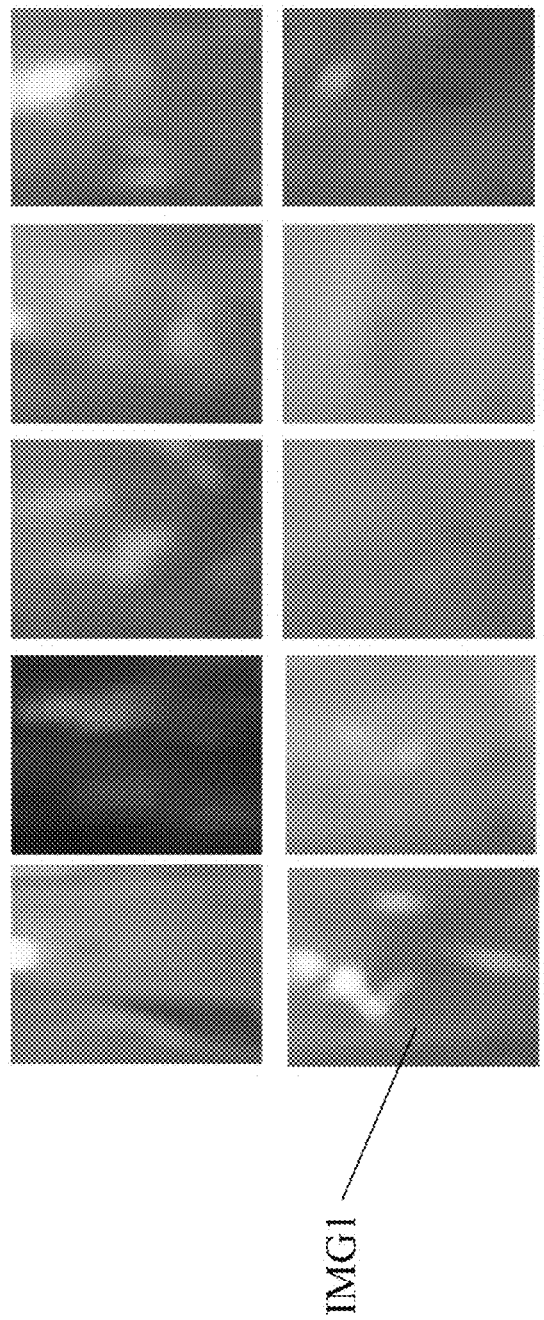
FIG. 4A to FIG. 4D respectively show images of waste liquids in different pipelines.
Figure 4B:
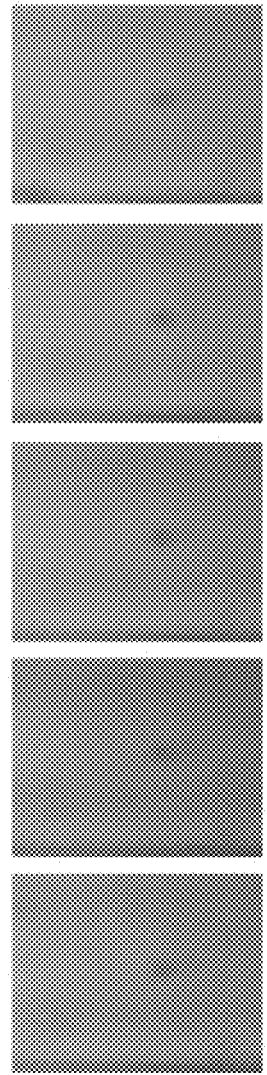
Figure 4C:
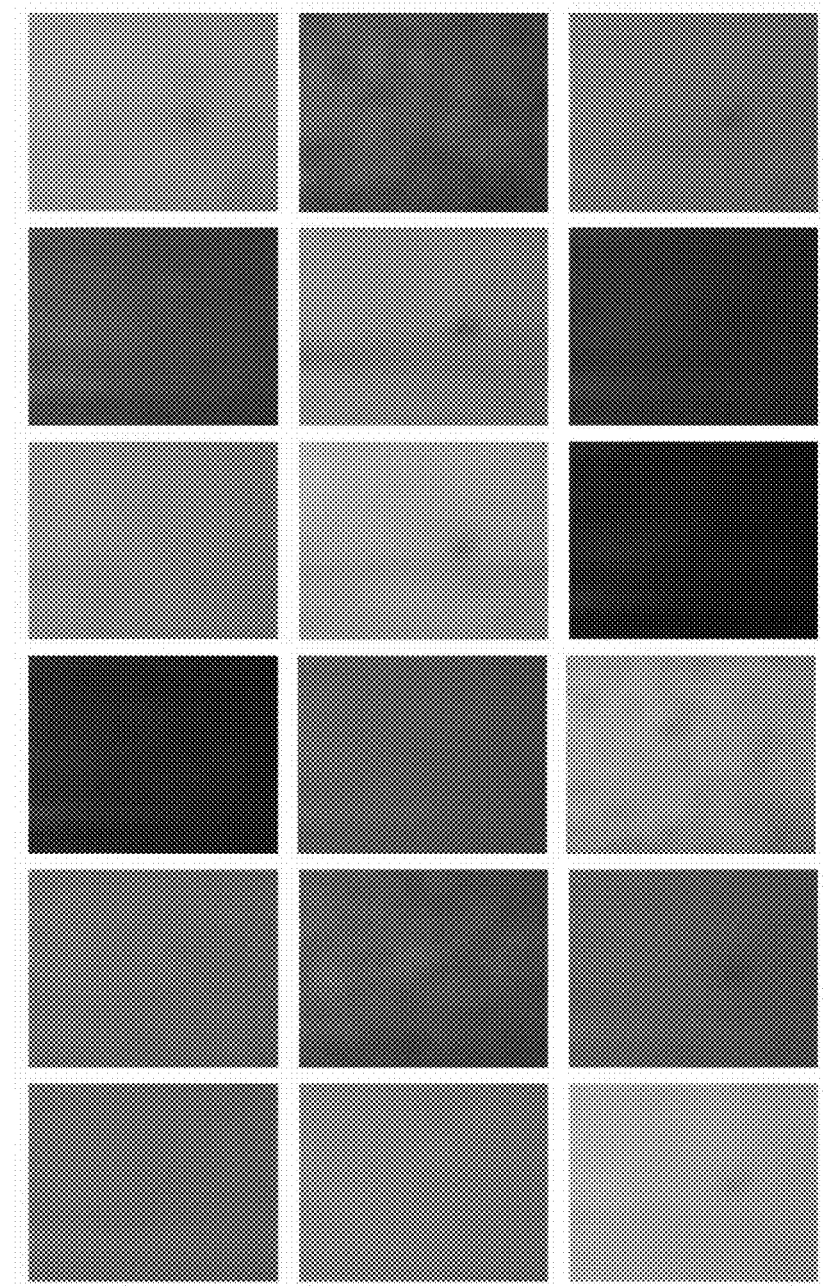
Figure 4D:
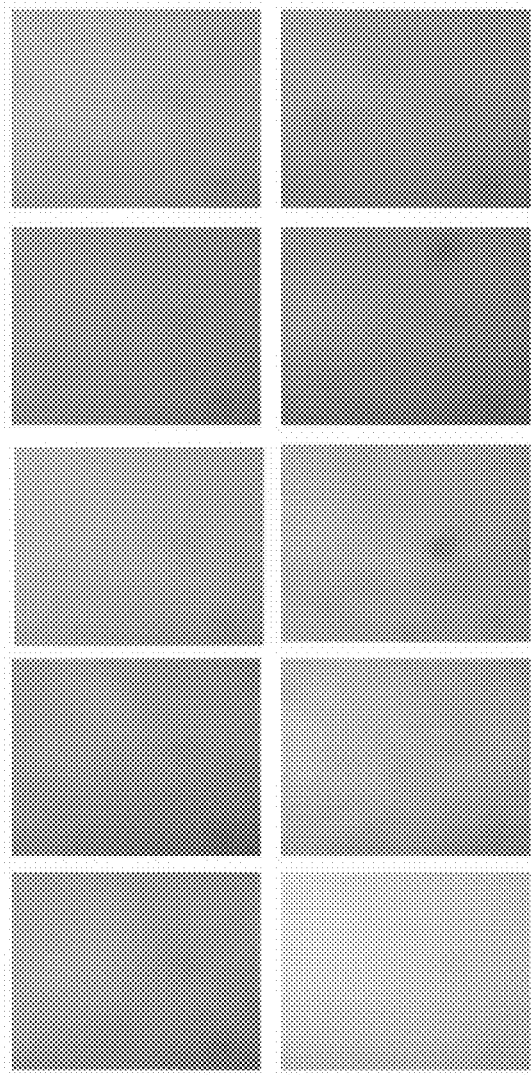

The following describes a method for establishing the statistical criteria. FIG. 3 is the flow schematic diagram of one embodiment of a method for establishing statistical criteria of the present disclosure. In some embodiments, the method 300 for establishing the statistical criteria can include a step 300a of providing a plurality of waste liquid images. FIG. 4A to FIG. 4D are respectively images of waste liquid in different transparent pipelines. FIG. 4A displays the images of waste liquid in the plurality of transparent pipelines when the waste liquid draining state is an empty draining state, namely the waste liquid at the bottom of the container A is drained by the draining device 20 and is mixed with air. FIG. 4B displays a plurality of images when no waste liquid passes through the transparent pipelines. FIG. 4C displays a plurality of images captured when a plurality of waste liquids with quality meeting the standard respectively pass through the transparent pipelines. FIG. 4D displays a plurality of images captured when a plurality of waste liquids with quality not meeting the standard respectively pass through the transparent pipelines. FIG. 4A to FIG. 4D above illustrates by taking a part of images as examples. In some embodiments, the number of the images required for establishing the statistical criteria can be up to tens of thousands, so that more accurate determination results can be obtained in subsequent training and learning.

Figure 5:
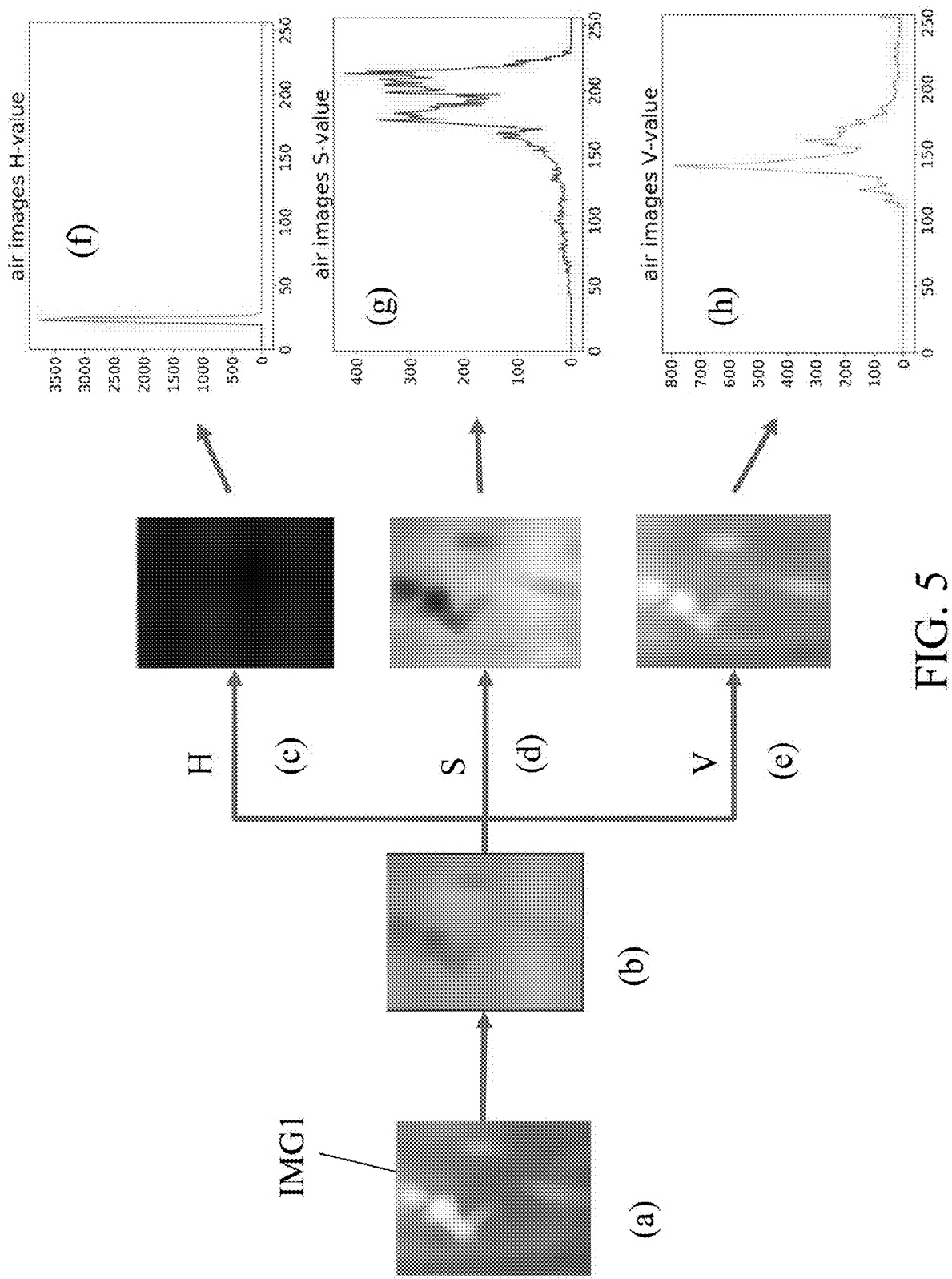
FIG. 5 is a schematic diagram of capturing characteristic data of each waste liquid image by HUV color characteristics.

The method 300 for establishing the statistical criteria can further include a step 300b of performing image processing on the plurality of waste liquid images to obtain a plurality of characteristic data of the color characteristics of each image. In some embodiments, the color characteristics can be selected from the group consisting of HSV characteristics, RGB characteristics, and a combination thereof. In some embodiments, the HSV characteristics can include huc (H), saturation (S) and value (V). The RGB characteristics can include color characteristics such as red (R), green (G) and blue (B). In some embodiments, the HSV color characteristics are illustrated by taking an image IMG1 in FIG. 4A as an example. As shown in FIG. 5, FIG. 5(a) shows the image IMG1, FIG. 5(B) shows a color space of transforming the image IMG1 in FIG. 5(a) into HSV, the transformation manner is a technology well known by those skilled in the art, and no more description is made herein. According to the principle of HSV color synthesis, the image IMG1 consists of an image representing H (as shown in FIG. 5 (c)), an image representing S (as shown in FIG. 5 (d)) and an image representing V (as shown in FIG. 5 (e)). Since each image has a plurality of pixels (e.g., 128×128 pixels), and the resolution of each image has corresponding H, S and V for each pixel, for the image representing H in FIG. 5(c), a curve of the number of pixels and the H shown in FIG. 5(f) can be formed. In FIG. 5(f), an abscissa represents H (e.g., from 0 to 255), and an ordinate represents the number of pixels. Similarly, for the image representing S (as shown in FIG. 5 (d)), a curve of the number of pixels and the V shown in FIG. 5(g) can be formed; and for the image representing V (as shown in FIG. 5 (e)), a curve of the number of pixels and the V shown in FIG. 5(h) can be formed.

Figure 6:
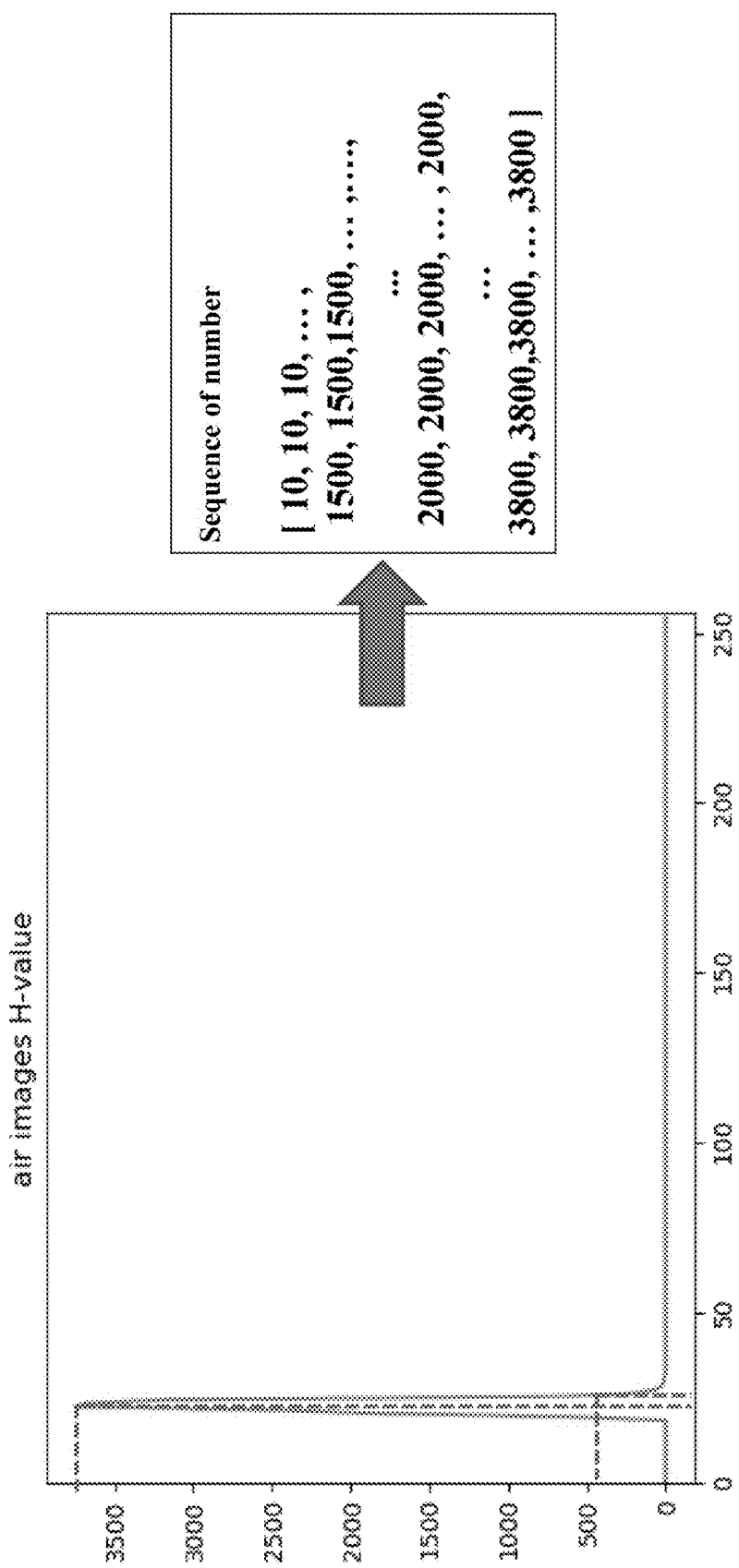
FIG. 6 is a schematic diagram of relationship between a number of pixels and a Hue (H) value.

The number of pixels of each image with the HSV above and corresponding numerical values can be further used for calculating the numerical values. FIG. 6 is the schematic diagram of relationship between a number of pixels and a Hue (H) value. By taking the H image of FIG. 5(c) for illustrating, the number of pixels corresponding to each H of the H image in FIG. 5(c) is counted to form characteristic data, for example, there are 10 pixels with H of 10, and there are 20 pixels with H of 3,800, the characteristic data can be formed after counting the number of all the pixels with H.

Figure 7:
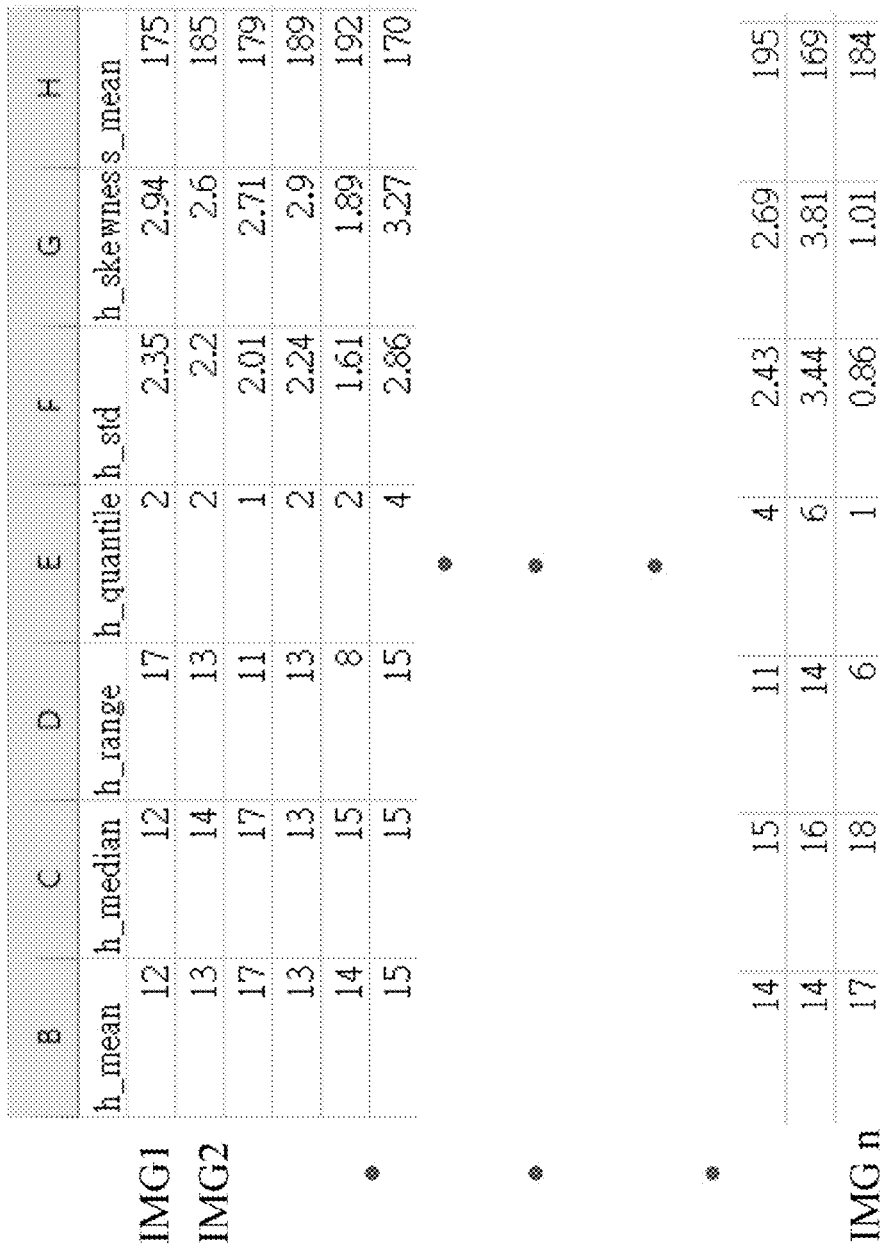
FIG. 7 is a HUV characteristic value list corresponding to each image.

FIG. 7 is the characteristic value list corresponding to each image. The method 300 for establishing the statistical criteria can further include a step 300c of performing statistical calculation processing on the plurality of characteristic data of each image to obtain a plurality of statistical characteristic values of each image. The step 300c includes obtaining a statistical data condition of the characteristic data through statistical calculation. The data condition can be selected from the group consisting of a data concentration trend, a data dispersion degree, a data distribution pattern, and a combination thereof. In some embodiments, the data concentration trend at least includes mean or median of the characteristic data. The data dispersion degree at least includes range, interquartile range or standard deviation of the characteristic data. The data distribution pattern at least includes skewness of the characteristic data. But it is not limited to the above six types. The above calculation formula of the various statistical counting values is defined by method well known by those skilled in the art, and no more description is made herein. In some embodiments, as shown in FIG. 7, the characteristic values calculated for an R image in each image is displayed, where h_mean represents the mean of H of each pixel in the H image, h_median represents the median of H of each pixel in the H image, h_range represents the range of H of each pixel in the H image, h_quantile represents interquartile range of H of each pixel in the H image, h_std represents standard deviation of H of each pixel in the H image, and h_skewness represents skewness of H of each pixel in the H image. For example, for each image, taking the IMG1 as an example, the H image of the IMG1 may contain above six characteristic values S. Similarly, an S image and a V image may respectively contain above six characteristic value. Therefore, after the step 300c. 18 characteristic values of each image can be obtained; and a big data database of the characteristic values corresponding to H, S and V can be established by collecting tens of thousands of and even hundreds of thousands of images.

Figure 8A:
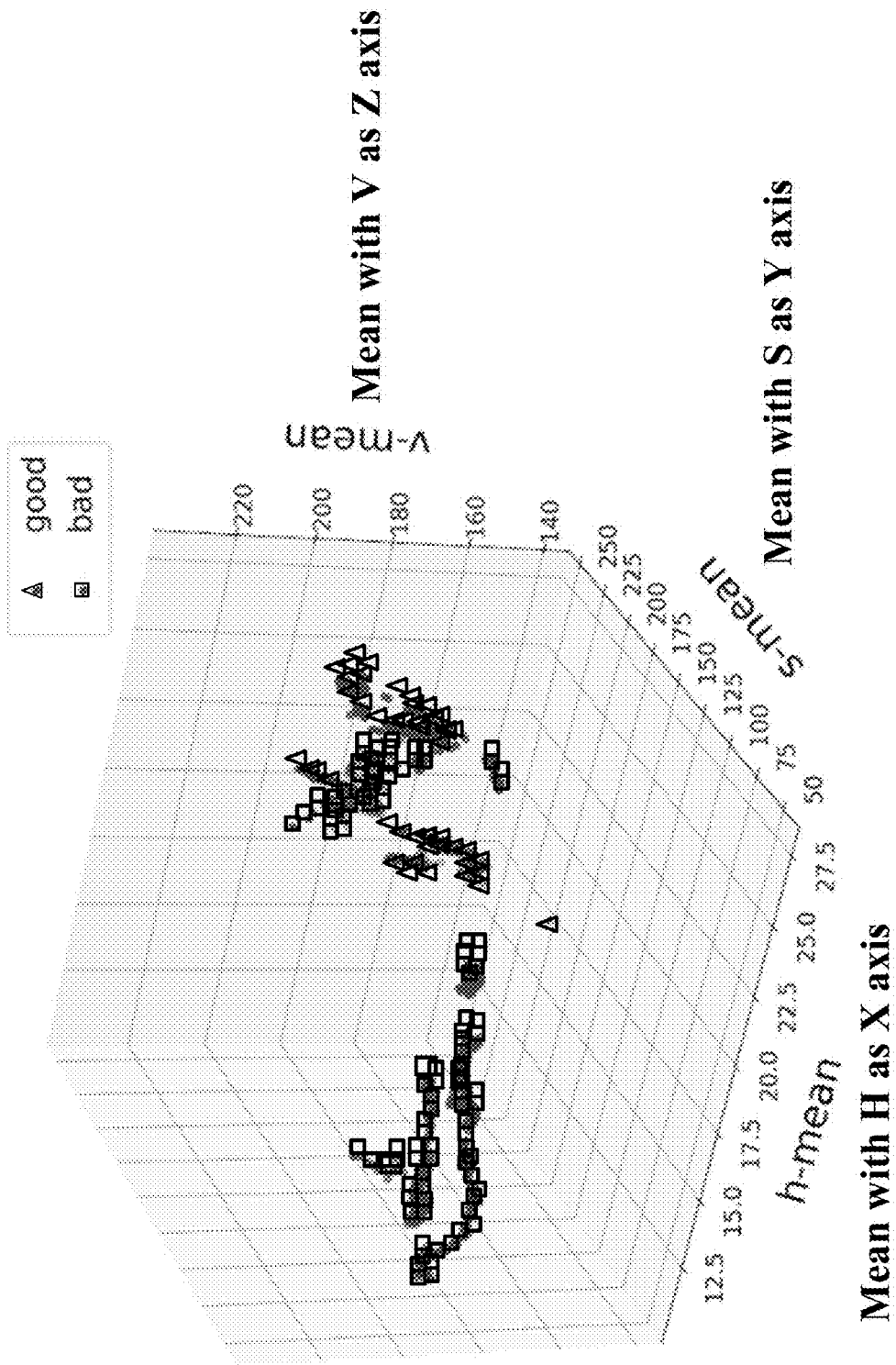
FIG. 8A is a three-dimensional characteristic data distribution diagram of a plurality of randomly selected images with waste liquid quality meeting a recycling standard and not meeting the recycling standard.
Figure 8C:
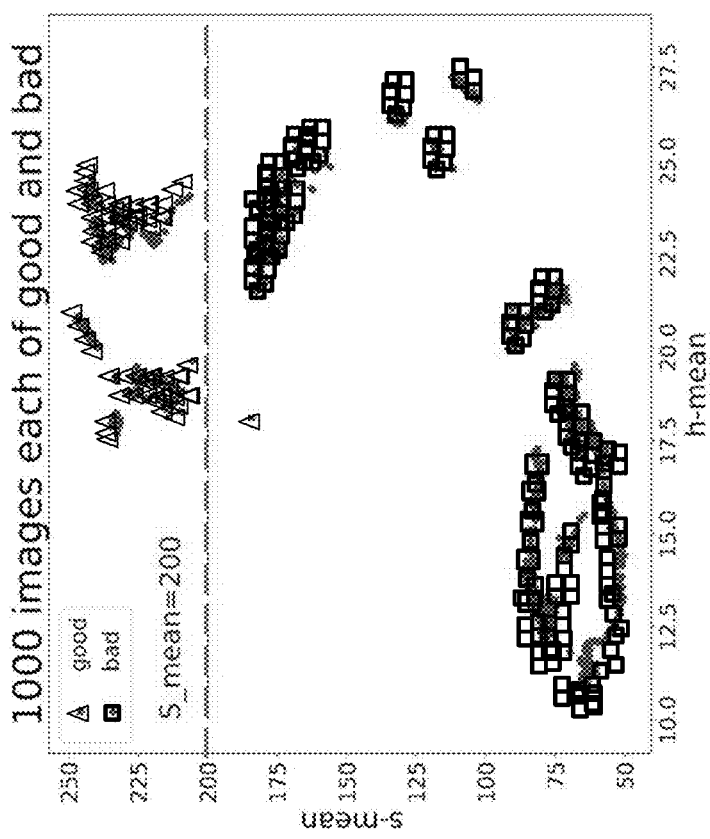
FIG. 8B and FIG. 8C are respectively characteristic data distribution diagrams of a three-dimensional characteristic data distribution diagram of FIG. 8A in different planes.

After the big data database is established, the method 300 for establishing the statistical criteria can further include a step 300d of establishing corresponding statistical criteria according to the statistical characteristic values of the same type in the plurality of waste liquid images. In some embodiments, the used statistical characteristic values can be of different types. In some embodiments, the statistical characteristic values may include but are not limited to mean of saturation (S), mean of hue (H), mean of value (V), mean of red (R), mean of green (G), mean of blue (B), median of saturation (S), median of hue (H), median of value (V), median of red (R), median of green (G), median of blue (B), skewness of saturation (S), skewness of hue (H), skewness of value (V), skewness of red (R), skewness of green (G), skewness of blue (B), standard deviation of saturation (S), standard deviation of hue (H), standard deviation of value (V), standard deviation of red (R), standard deviation of green (G), standard deviation of blue (B), interquartile range of saturation (S), interquartile range of hue (H), interquartile range of value (V), interquartile range of red (R), interquartile range of green (G), interquartile range of blue (B), range of saturation (S), range of hue (H), range of value (V), range of red (R), range of green (G), or range of blue (B). In some embodiments, the method for establishing can be that the characteristic values in the big data database generated in the step 300c can be trained through an artificial intelligence algorithm. An artificial intelligence model for training can be, but is not limited to, a convolutional neural network (CNN) model or an extreme gradient boosting (XGBoost) model. In some embodiments, the selected model is used for training by taking the mean of H, S and V of the plurality of images as the statistical characteristic values so as to establish the statistical criteria for determining whether the waste liquid quality meets the recycling standard and does not meet the recycling standard. FIG. 8A is a centralized trend diagram of characteristic data of a plurality of randomly selected images with waste liquid quality meeting a recycling standard and not meeting the recycling standard, in the figure, u represents the statistical characteristic value of the unqualified waste liquid, and A represents the statistical characteristic value of the qualified waste liquid. In this embodiment, 1,000 images are provided for illustrating, but it is not limited by those, and the mean of the corresponding H, the mean of the corresponding S and the mean of the corresponding V are respectively marked in X, Y and Z space coordinates respectively. X axis represents the mean of H, the Y axis represents the mean of S, and the Z axis represents the mean of V.

Figure 8B:
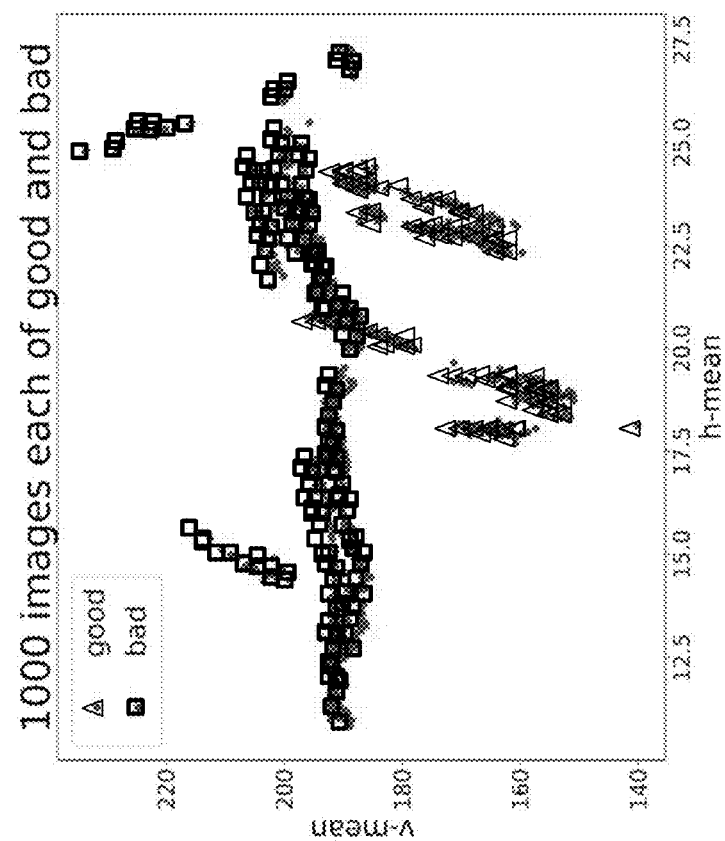
Figure 8D:
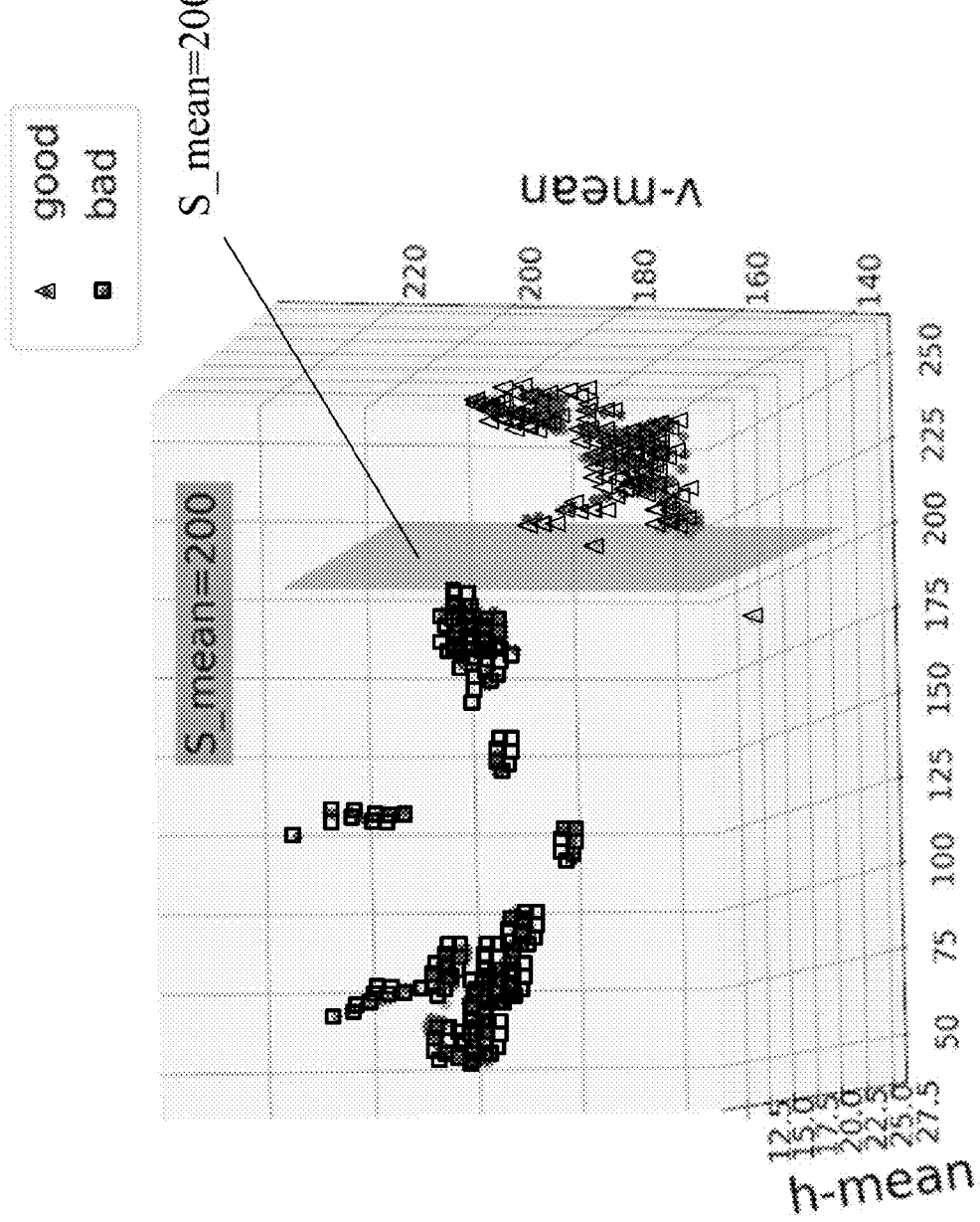
FIG. 8D is a schematic diagram for separating three-dimensional characteristic data distribution in FIG. 8A by statistical criteria.

Under the X, Y and Z space coordinates shown in FIG. 8A, according to the data space distribution of the mean of each of H, S and V, it cannot completely separate unqualified waste liquid (□) from qualified waste liquid (Δ). However, from the perspective of each plane, for example, as shown in FIG. 8B, from the perspective of the two-dimensional distribution of the mean of H and the mean of V in an XZ plane (front view of FIG. 8A), the data of □ and the data of Δ are intersected and cannot be separated. However, from the perspective of the two-dimensional distribution of the mean of H and the mean of S in, for example, an XY plane (overlook of FIG. 8A), the data of □ and the data of Δ are obviously separated when the mean of S is 200. Therefore, the statistical characteristic value (e.g., the mean of S) can also be referred to as "separated statistical characteristic value." A position where the mean of the S is 200 can be found through the training model, and thus the quality of the qualified waste liquid and the quality of the unqualified waste liquid can be obviously separated in data. Therefore, as shown in FIG. 8D, in the three-dimensional space of FIG. 8A, a plane Y=200 can be drawn when the mean of the S is 200, and the quality of the qualified waste liquid and the quality of the unqualified waste liquid can be perfectly distinguished based on the plane Y=200, thus that the mean of S is 200 is the statistical criterion obtained after training. In other words, that the mean of S is 200 can be regarded as the statistical criterion obtained by training by taking the mean of H, the mean of S and the mean of V as the data space. In some embodiments, the statistical criterion can also be referred to as "separated statistical criterion."

According to the above method for establishing the statistical criteria, data analysis and training learning can be sequentially carried out on other statistical characteristic values (such as median, range, interquartile range, standard deviation or skewness of S, median, range, interquartile range, standard deviation or skewness of H, and median, range, interquartile range, standard deviation or skewness of V), thus a division plane corresponding to a boundary value capable of distinguishing the quality of qualified waste liquid from the quality of unqualified waste liquid can be found out, and the division plane can be used as the statistical criterion.

Figure 9A:
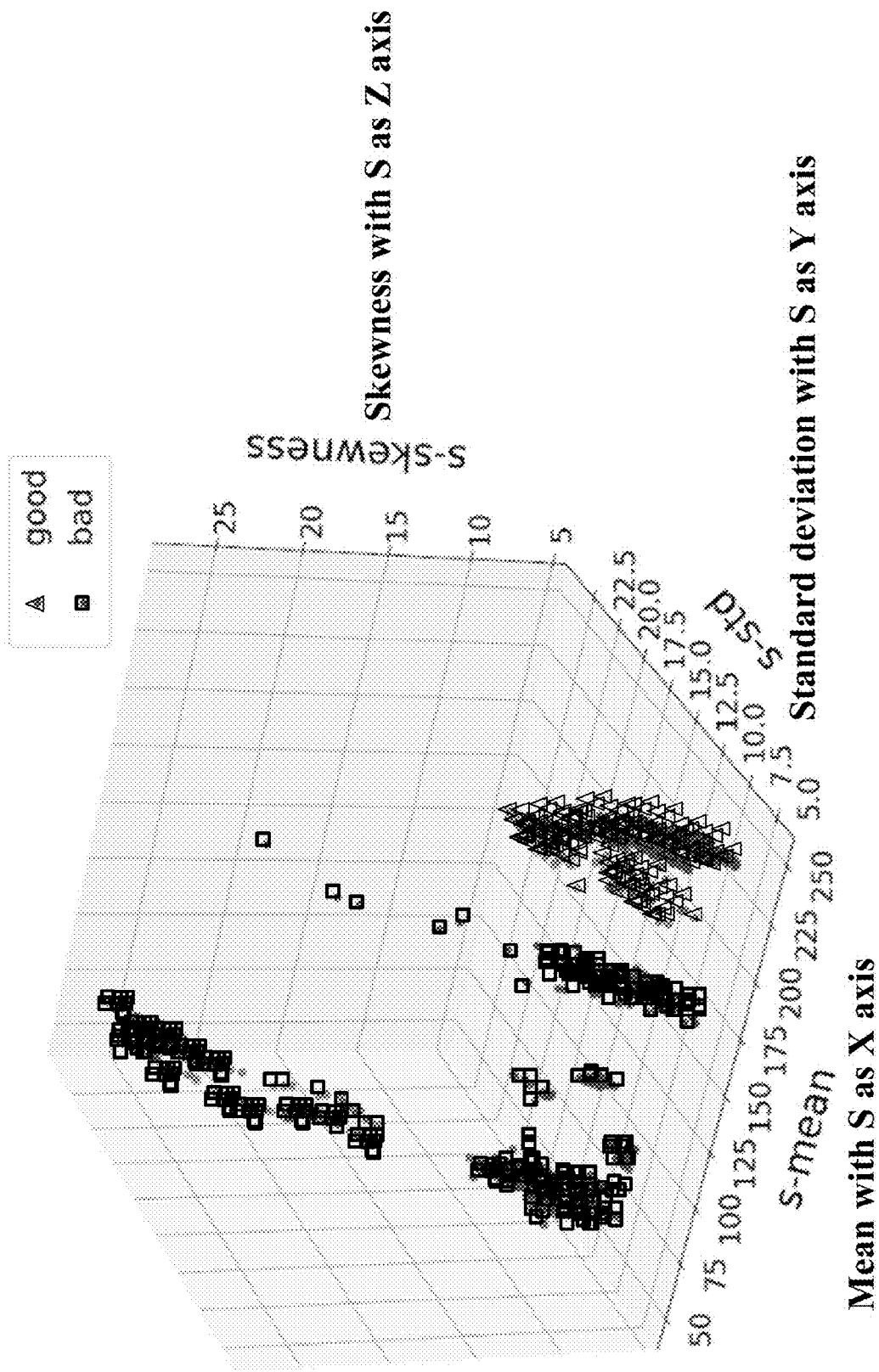
FIG. 9A is another embodiment distribution diagram of three-dimensional characteristic data of a plurality of randomly selected images with waste liquid quality meeting a recycling standard and not meeting the recycling standard.
Figure 9B:
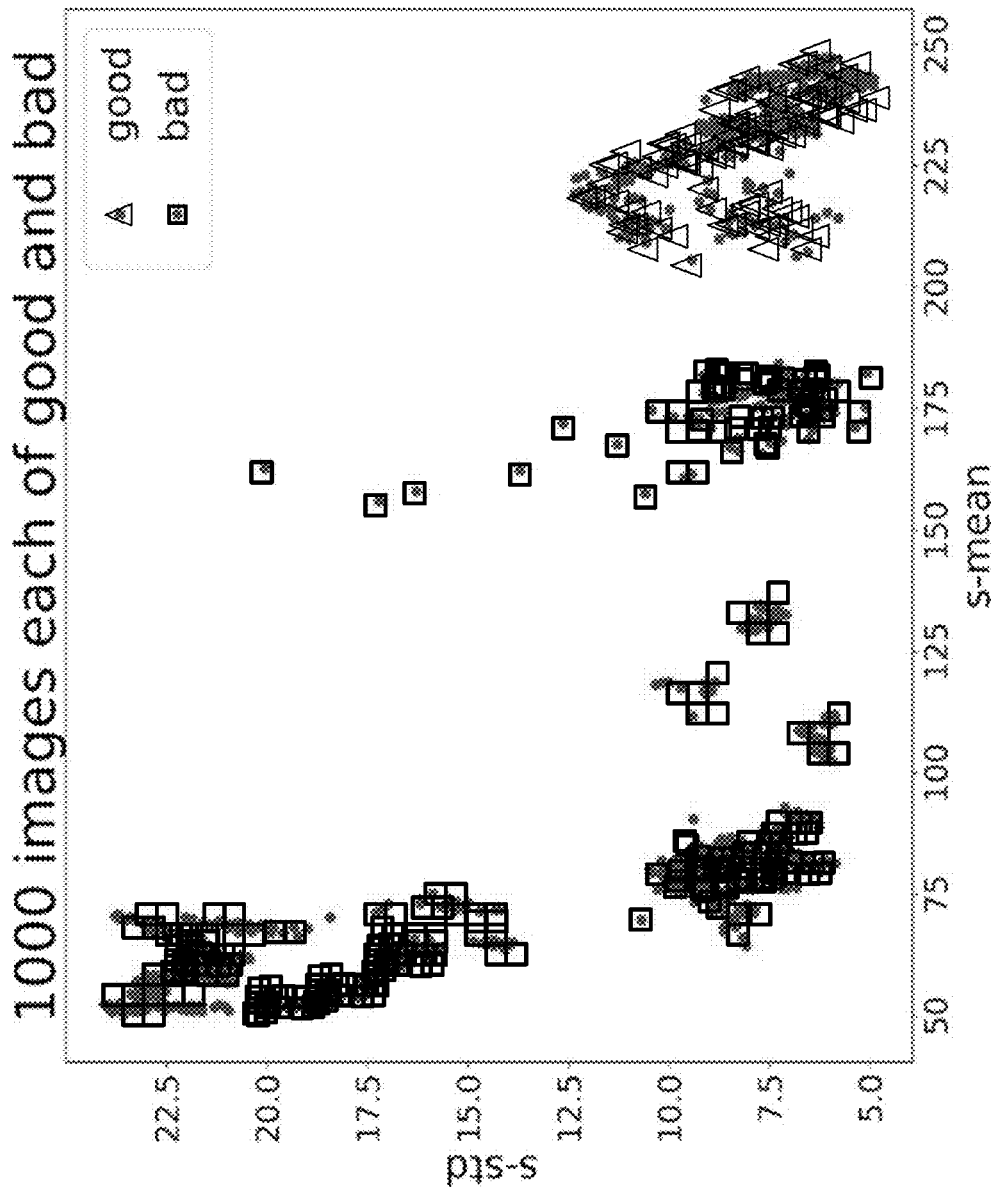
FIG. 9B is a distribution diagram of characteristic data of a three-dimensional characteristic data distribution diagram in FIG. 9A in a specific plane.
Figure 9C:
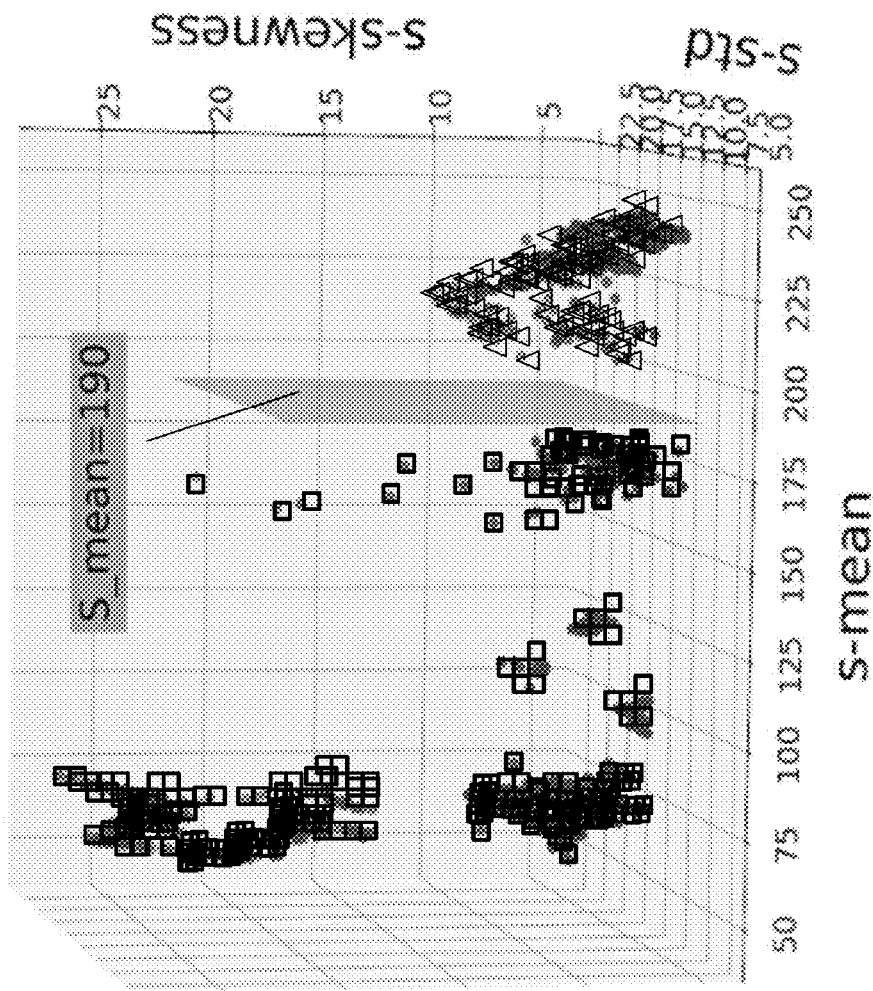
FIG. 9C is a schematic diagram for separating three-dimensional characteristic data distribution in FIG. 9A by statistical criteria.

In some embodiments, training and learning can be performed in the three-dimensional space to find out the statistical criteria by different statistical characteristic value combination. For example, as shown in FIG. 9A to FIG. 9C, in the three-dimensional space of statistical characteristic values shown in FIG. 9A, the X axis represents the mean of S, the Y axis represents the standard deviation of S, and the Z axis represents the skewness of S. FIG. 9A shows the data space distribution established by the mean, the standard deviation and the skewness of each S, the unqualified waste liquid (□) and the qualified waste liquid (Δ) cannot be completely separated. However, from the perspective of each plane, for example, as shown in FIG. 9B, it can be clearly seen from the two-dimensional distribution of the mean of S and the standard deviation of S under the XY plane (overlooked in the FIG. 9A) that the data of □ and the data of Δ can be clearly distinguished when the mean of S is 190. A position where the mean of S is 190 can be found out by the training model, and thus the quality of the qualified waste liquid and the quality of the unqualified waste liquid can be obviously separated in data. Therefore, as shown in FIG. 9C, a plane X=190 can be drawn when the mean of S is 190 in the three-dimensional space of FIG. 9A, and the quality of the qualified waste liquid and the quality of the unqualified waste liquid can be perfectly distinguished by dividing through the plane X=190, thus that the mean of the S is equal to 190 can be regarded as the statistical criterion obtained by training by taking the mean of the S, the standard deviation of S and the skewness of S as the data space. It is to be noted that the mean of the S serving as the statistical criterion is not limited by 190, and in some embodiments, the mean of the S serving as the statistical criterion can be 189-228. In addition, in some embodiments, the mean of H serving as the statistical criterion can be 16-22. In some embodiments, the mean of V serving as the statistical criterion can be 145-173. In some embodiments, the standard deviation of S serving as the statistical criterion can be 6.92-10.44. In addition, in some embodiments, the standard deviation of hue H serving as the statistical criterion can be 0.45-0.66. In some embodiments, the standard deviation of S serving as the statistical criterion can be 8.51-11.47. It is to be noted that the foregoing scope is only an embodiment of the present disclosure, which is changed according to the national or regional habits and types of oil used.

In some embodiments, the empty draining state shown in FIG. 4A and the statistical criterion for image separation when no waste liquid passes through the transparent pipeline shown in FIG. 4B can also adopt the same manner above, the big database and the artificial intelligence training model are used for training and distinguishing the empty draining state and the state when no waste liquid passes through the transparent pipeline, the manner is the same as the above, and no more description is made herein. In some embodiments, the statistical criterion can also be established by the color characteristics of RGB, and the establishment manner is as follows.

Figure 10:
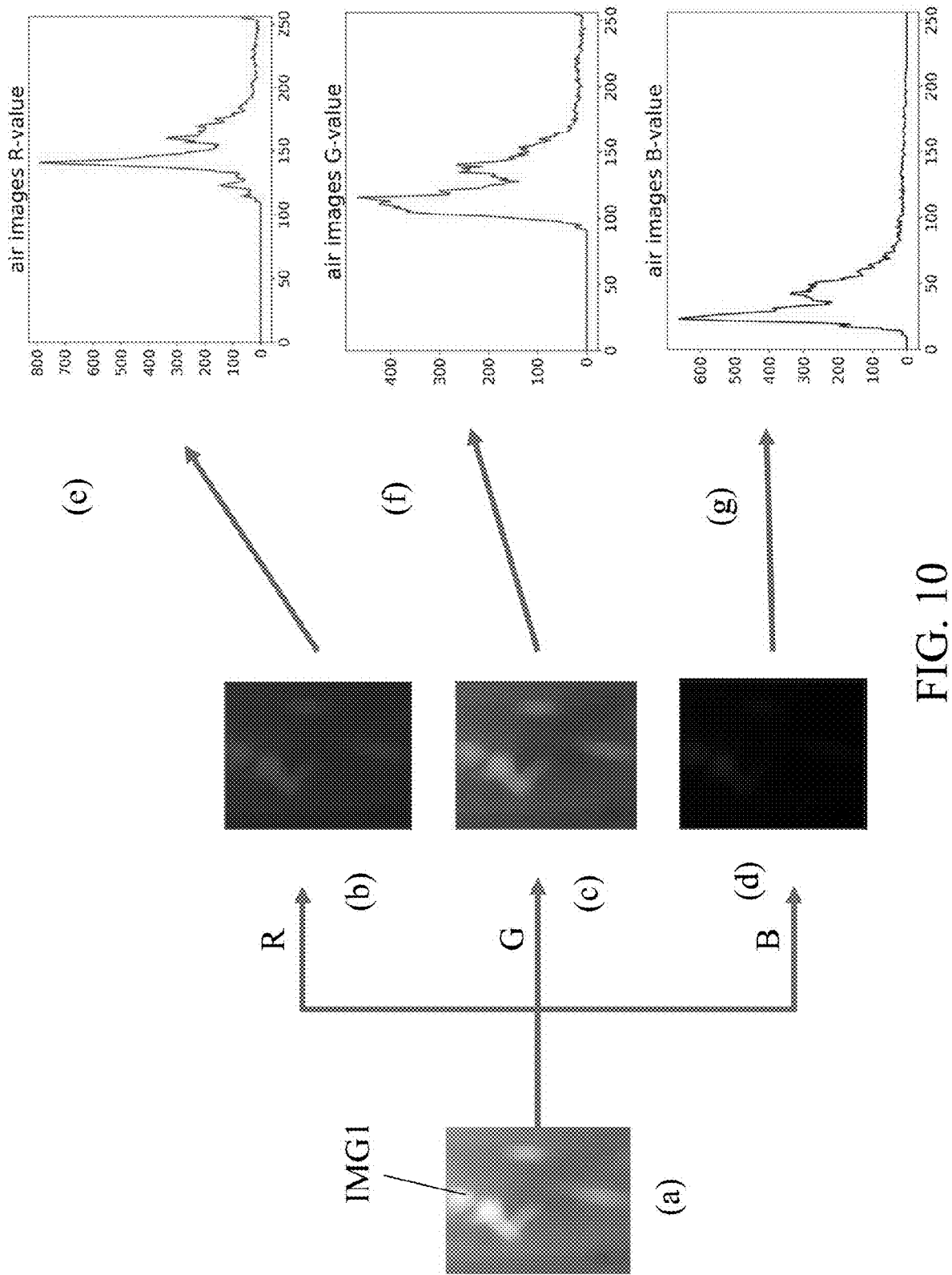
FIG. 10 is a schematic diagram of capturing characteristic data of each waste liquid image by RGB color characteristics.

The characteristics of RGB color are illustrated by taking the image IMG1 in FIG. 4B as an example. As shown in FIG. 10, FIG. 10(a) displays the image IMG1, and according to the principle of RGB color synthesis, the image IMG1 consists of an image representing R (shown in FIG. 10 (B)), an image representing G (shown in FIG. 10 (c)) and an image representing B (shown in FIG. 10 (d)). Each image has a plurality of pixels, and each pixel has corresponding R, G and B values, so a curve of the number of the pixels and the R value shown in FIG. 10 (c) can be formed for the R image in FIG. 10(B). In FIG. 10(c), an abscissa represents the R value (for example: from 0 to 255), and an ordinate represents the number of the pixels. Similarly, a curve of the number of the pixels and the G value shown in FIG. 10(f) can be formed for the G image in FIG. 10(c), and a curve of the number of the pixels and the B value shown in FIG. 10 (G) can be formed for the B image in FIG. 10(d).

Figure 11:
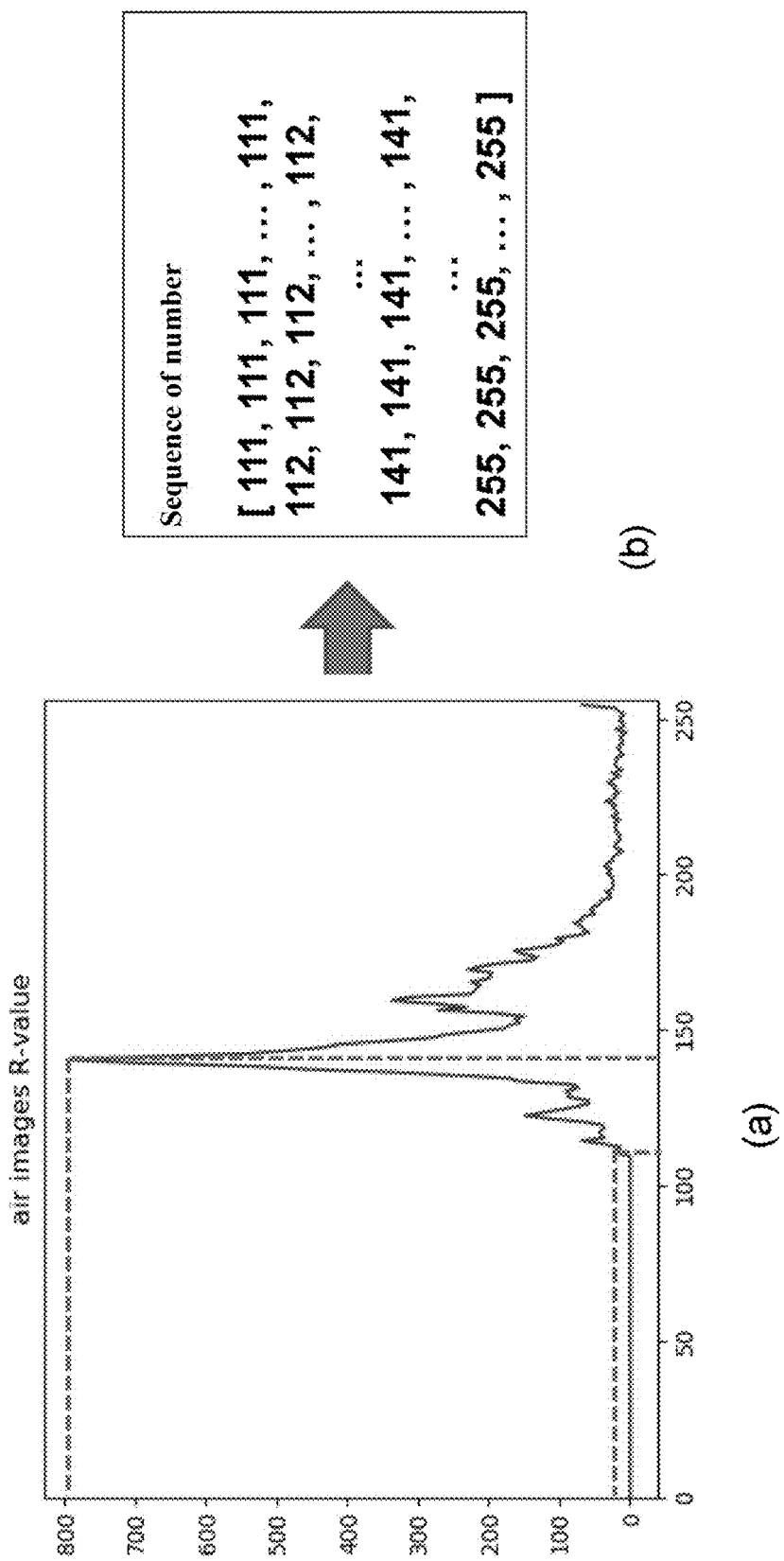
FIG. 11 is a schematic diagram of relationship between a number of pixels and a color R value.

The number of pixels of each image with the RGB above and corresponding numerical values can be further used for calculating the numerical values. FIG. 11 is the schematic diagram of relationship between a number of pixels and a color R value. By taking the R image in FIG. 10(b) for illustrating, the number of pixels corresponding to each R value of the R image in FIG. 10(b) is counted to form the characteristic data, for example, there are 21 pixels with the R value of 111, and there are 790 pixels with the R value of 141, the characteristic data can be formed by counting the number of all the pixels with R value. Then, the plurality of characteristic data of each image are calculated to obtain the plurality of statistical characteristic values of each image.

FIG. 12 is the characteristic value list corresponding to each image. Statistical calculation is performed according to the characteristic data obtained in the above step 300b so as to obtain the statistical data condition of the characteristic data, where the data condition can be selected from the group consisting of the data concentration trend, the data dispersion degree, the data distribution pattern, and the combination thereof. In some embodiments, the data concentration trend at least includes the mean or the median of the characteristic data; the data dispersion degree at least includes range, interquartile range or standard deviation of the characteristic data: and the data distribution pattern at least include skewness and the like of the characteristic data. But it is not limited to the above six types. In some embodiments, FIG. 12 shows the characteristic values calculated by the R image in each image, where r_mean represents the mean of R of each pixel in the R image, r_median represents the median number of R of each pixel in the R image, r_range is the range of R of each pixel in the R image, r_quantile is the interquartile range of R of each pixel in the image, r_std is the standard deviation of R of each pixel in the R image, and r_skewness is the skewness value of R of each pixel in the image. For each image, for example, IMG1 is taken as an example, and the R image of the IMG1 may include the above six characteristic values. Similarly, G and B images may also include the above six characteristic values respectively. Therefore, after the step 300c, 18 characteristic values of each image can be obtained, and a big data database of the characteristic values can be established by collecting tens of thousands of and even hundreds of thousands of images.

After the big data database is established, the above step 300d can be carried out. In some embodiments, the method for establishing can train the characteristic values above in the generated big data database through the artificial intelligence algorithm. An artificial intelligence model for training can be, but is not limited to, a CNN model or an XGBoost model. In some embodiments, the training learning mode can be the same as the mode in FIG. 8A to FIG. 9C above, and the difference only lies in that the statistical characteristic value of HSV is changed into the statistical characteristic value of RGB.

After the method for establishing the statistical criteria is illustrated, as shown in FIG. 1 and FIG. 2, in some embodiments, the method 3 for recycling can further include a step 31 of draining the waste liquid 90 by the draining device 20 of the apparatus 2 for waste liquid recycling, enabling the waste liquid 90 to pass through the transparent pipeline 202, and capturing an image of the waste liquid in the transparent pipeline 202 by the image capturing device 22 arranged on one side of the transparent pipeline 202.

In some embodiments, the method 3 for recycling can further include a step 32 of performing image processing on the image of the waste liquid through the operation processing device 24 to obtain a plurality of characteristic data about the color characteristic. In some embodiments, the color characteristic can be red (R), green (G) or blue (B) characteristic or hue (H), saturation (S) or value (V) characteristic. The procedure of the step 32 is to process the waste liquid image in a manner shown in the above step 300b, and the difference is that the waste liquid image is processed in the step 300b, the step 32 is to process the waste liquid image captured in an actual waste liquid recycling process, objects are different, but the processing procedures are the same, and no more description is made herein. The plurality of characteristic data relative to the captured waste liquid image obtained in the step 32 is like a sequence of number generated in FIG. 6, because the characteristics are the huc (H), saturation (S) or value (V) characteristic, the number of pixels under different H, the number of pixels under different S and the number of pixels under different V can be generated after the step 32.

In some embodiments, the method 3 for recycling can further include a step 33 of performing statistical calculation processing on the plurality of characteristic data through the operation processing device 24 to obtain a plurality of statistical characteristic values. The calculation processing in the step 33 is statistical calculation processing, and the characteristic data obtained in the step 32 are subjected to statistical calculation to obtain the mean, the median, the range, the interquartile range, the standard deviation and the skewness of H, the mean, the median, the range, the interquartile range, the standard deviation and the skewness of S, and the mean, the median, the range, the interquartile range, the standard deviation and the skewness of V. For each captured waste liquid image in the process of draining the waste liquid, 18 statistical characteristic values can be generated after the step 33.

In some embodiments, the method 3 for recycling can further include a step 34 of selecting at least one statistical criterion from the plurality of statistical criteria to compare with the statistical characteristic values through the operation processing device 24 so as to determine the quality of the waste liquid passing through the transparent pipeline. In some embodiments, for example, the above examples are illustrated by the HUV color characteristic, the operation processing device 24 selects the mean 190 of S as the statistical criterion to form a cutting plane, and for example, as shown in FIG. 8D, the waste liquid corresponding to the image with the mean of S less than 200 is unqualified waste liquid, and the waste liquid corresponding to the waste liquid image with the mean of S more than 200 is qualified waste liquid. Therefore, if the mean of S of the waste liquid image obtained in the step 33 is less than 200, the waste liquid is unqualified, otherwise, the waste liquid is qualified. It is to be noted that the statistical characteristic values selected in the step 34 is not taken as a single example, and it can be combined in various ways.

For example, in a determination embodiment, the quality of the waste liquid can be determined according to a first statistical criterion; if the waste liquid is qualified under the statistical criterion, whether the waste liquid in the transparent pipeline is qualified or not is determined according to a second statistical criterion; and a result of passing the two quality tests is used as a basis of the qualified waste liquid. For example, if the waste liquid does not pass the first test, or the waste liquid passes the first test and does not pass the second test, the waste liquid is regarded as unqualified waste liquid; and the determination accuracy can be improved through multiple statistical criteria.

Figure 13A:
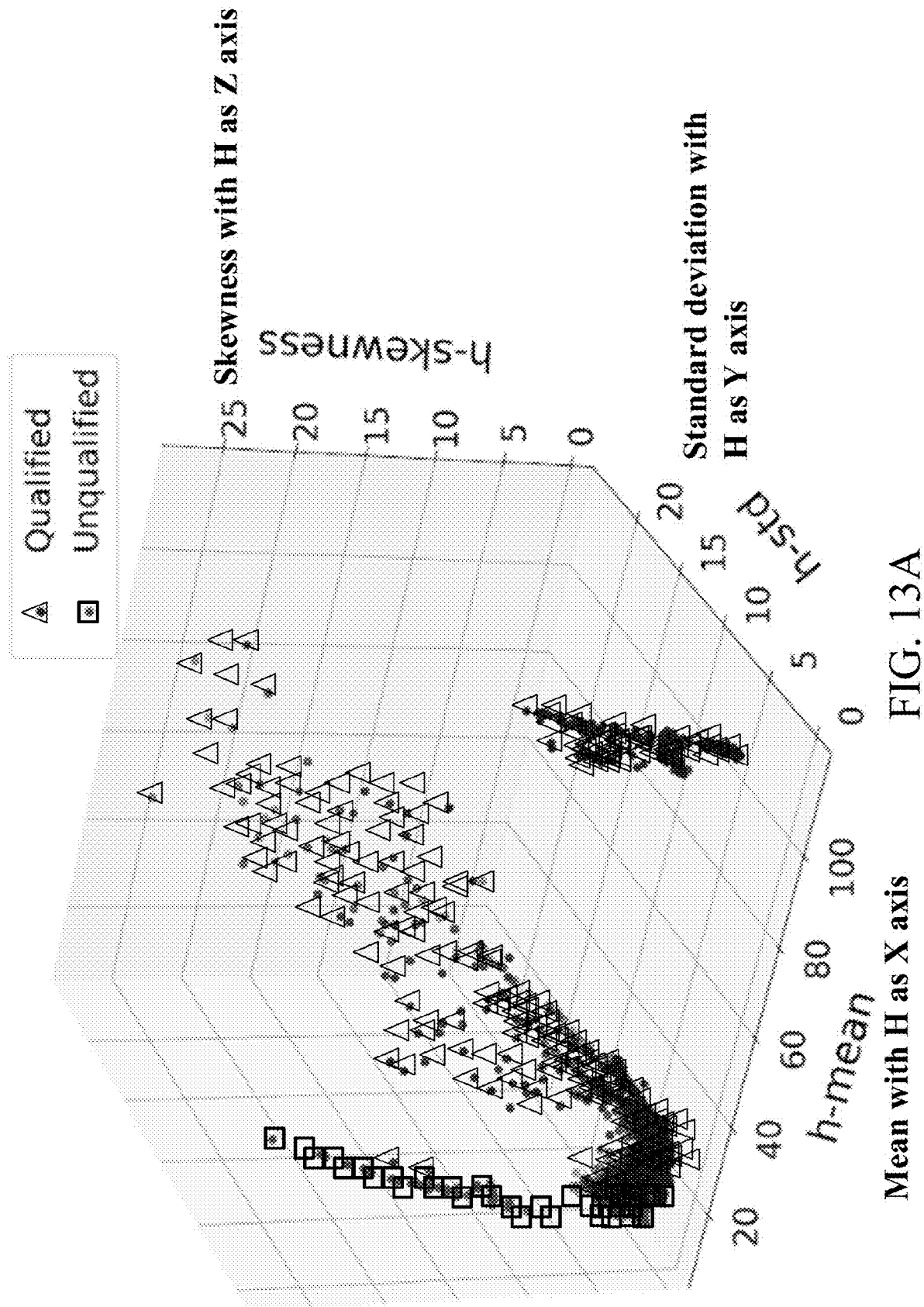
FIG. 13A-FIG. 13E are schematic diagrams for determining quality of waste oil by two statistical criteria.
Figure 13B:
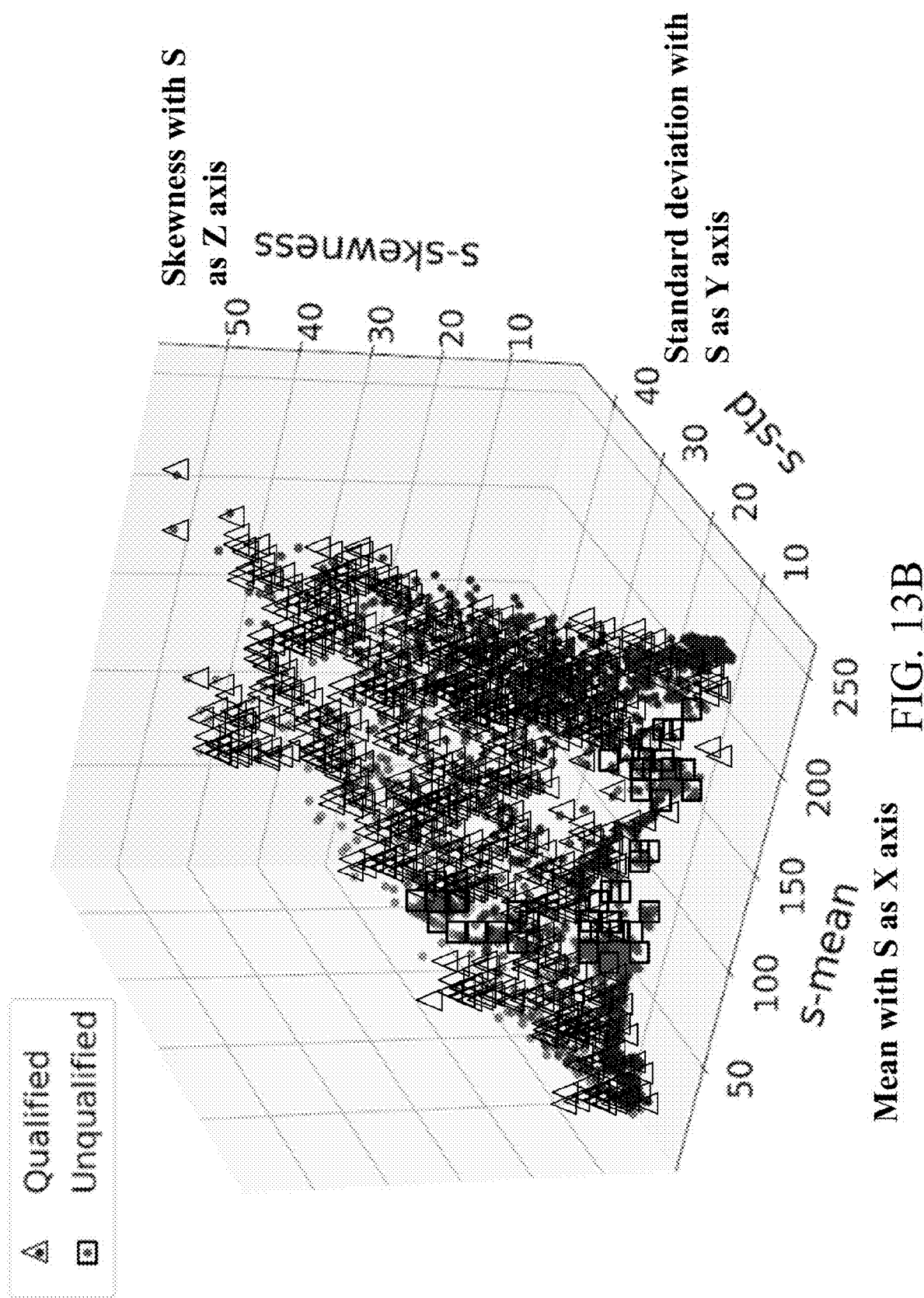
Figure 13C:
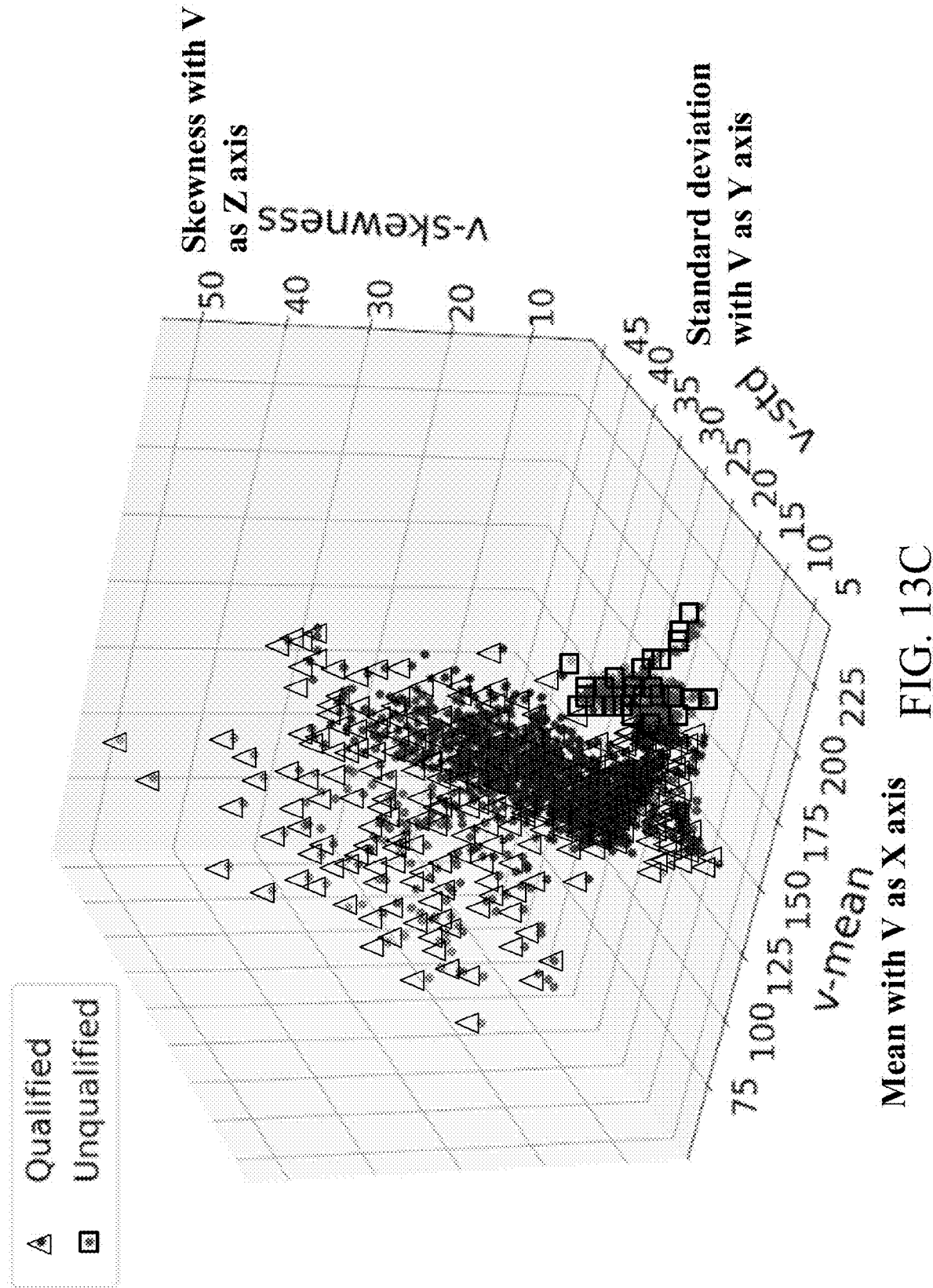

For example, in some embodiments, FIG. 13A-FIG. 13E are schematic diagrams for determining quality of waste oil by two statistical criteria. In some embodiments, in the figures, represents unqualified waste liquid, and A represents qualified waste liquid. In FIG. 13A, a space is established by statistical characteristic values, means, standard deviations and skewness of H in HSV of a plurality of images. In FIG. 13B, a space is established by statistical characteristic values, means, standard deviations and skewness of S in HSV of a plurality of images. In FIG. 13C, a space is established by statistical characteristic values, means, standard deviations and skewness of V in HSV of a plurality of images. As shown in FIG. 13A to FIG. 13C, the statistical characteristic values of the qualified waste liquid and the unqualified waste liquid are mixed together and are difficult to distinguish.

Figure 13D:
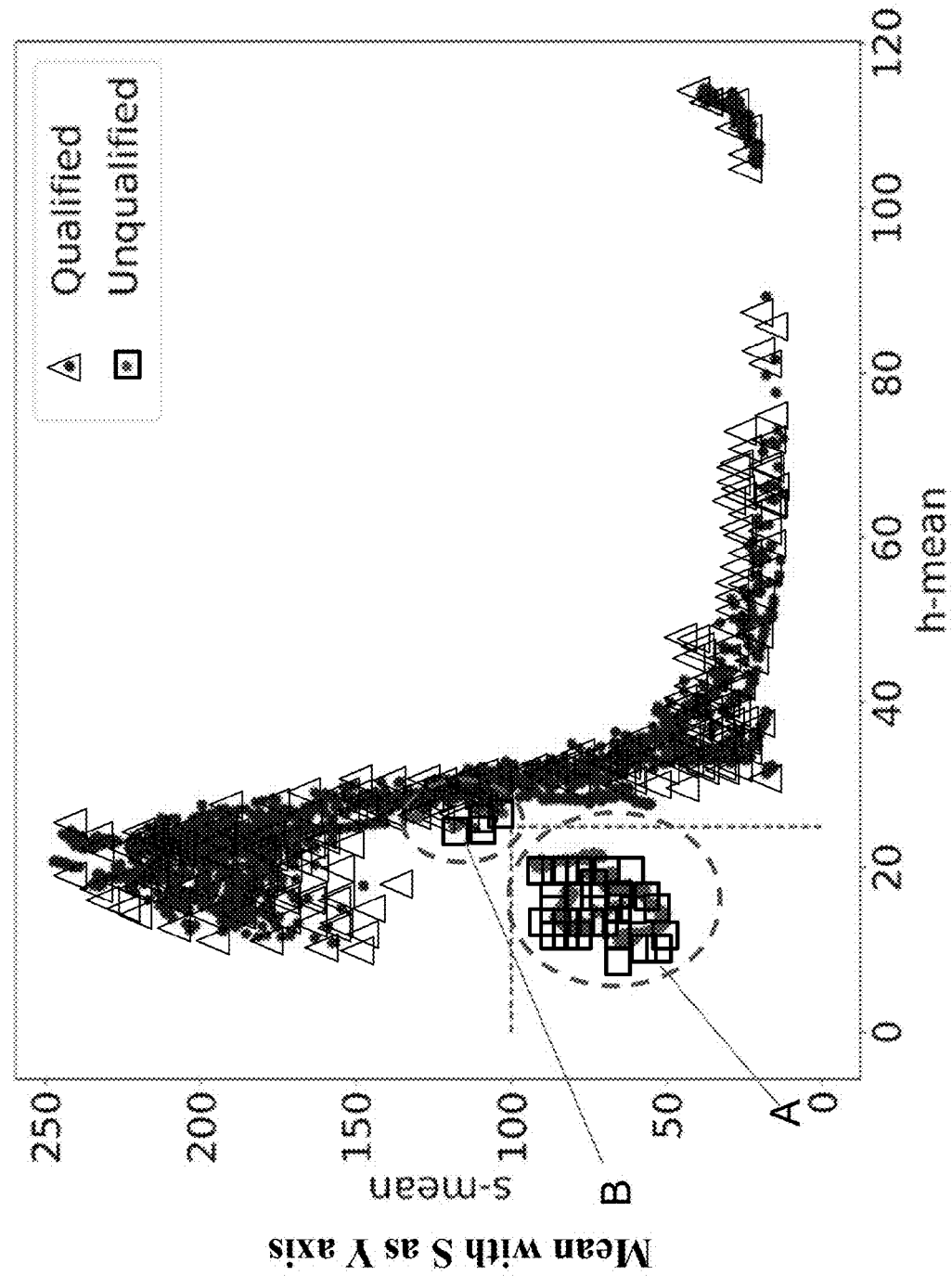
Figure 13E:
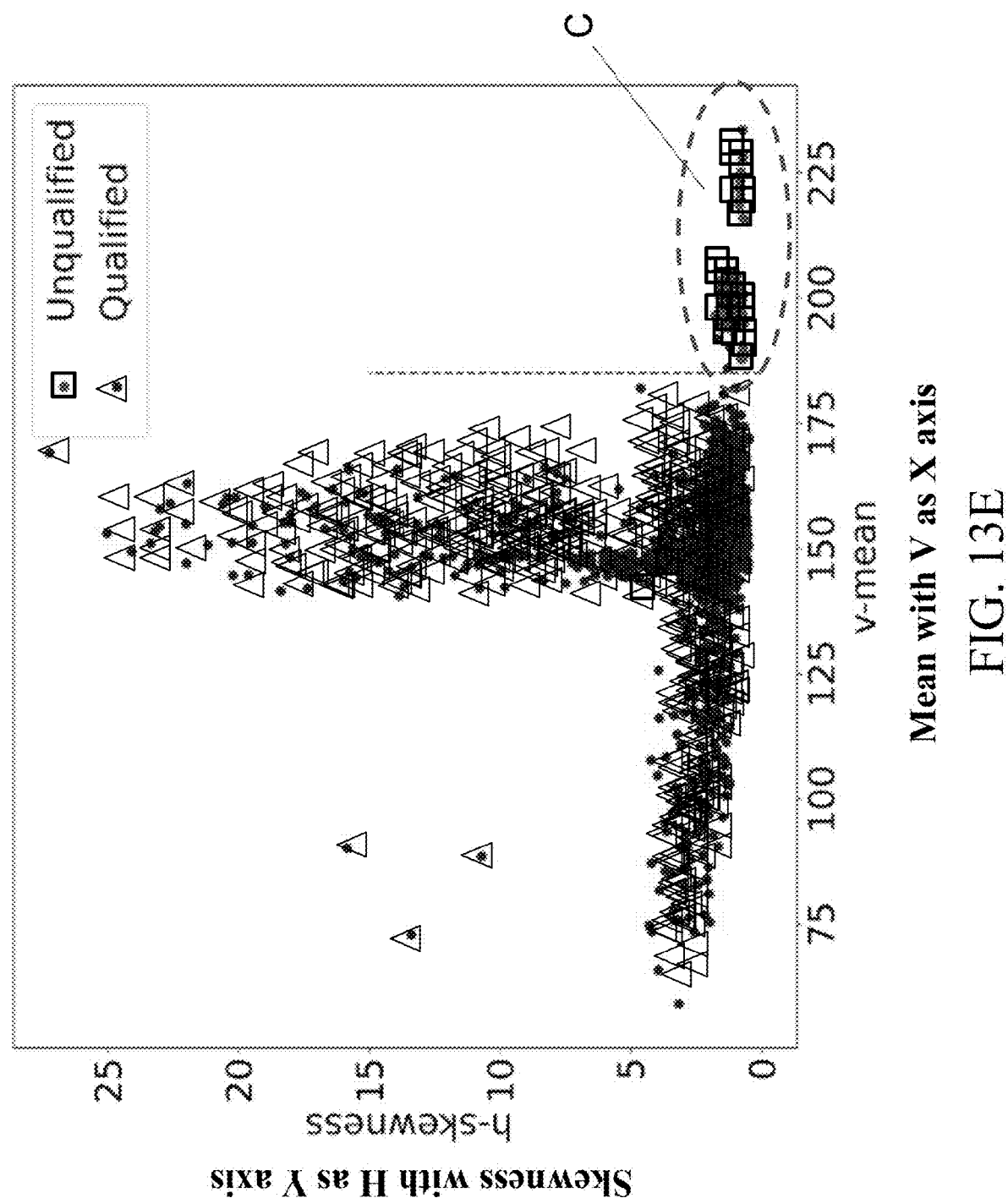

In some embodiments, the statistical mean of His used as the X axis, and the statistical mean of S is used as the Y axis to form a data distribution state as shown in FIG. 13D. It can be seen from the figure that unqualified waste liquid in the area A can be separated by statistical criteria established between the mean of H of 24-25 and the mean of S of 100-102, and data of the unqualified waste liquid can be filtered. Then, different coordinate system planes are switched, as shown in FIG. 13E, the statistical mean of V is used as the X axis, and the statistical skewness of H is used as the Y axis to form the data distribution state, it can be seen from the figure that unqualified waste liquid in an area C can be separated by statistical criteria established between the mean of V of 185-187, and the data of the unqualified waste liquid can be filtered. According to the above embodiments, the quality of the waste liquid can be determined by the first statistical criterion of the mean of H of 24-25 and the mean of S of 100-102, if the waste liquid is the qualified waste liquid under the statistical criteria, whether the waste liquid in the transparent pipeline is qualified waste liquid or not is determined according to the second statistical criterion of the mean of V of 185-187, and then the result of passing two quality tests is used as the basis of the qualified waste liquid.

In some embodiments, in order to improve the accuracy, the image capturing device in the step 31 is a high-speed image capturing device, and can be used for capturing a plurality of images in unit time. Therefore, in the step 32, a plurality of characteristic data corresponding to each waste liquid image can be generated. Then, in the calculation in step 33, a plurality of statistical characteristic values corresponding to each waste liquid image can be generated. In the above embodiments, each waste liquid image may have 18 statistical characteristic values. Then, in the determination of the step 34, a threshold value for passing through the statistical criterion can be set under the selected statistical criterion, and the waste liquid with the waste liquid image exceeding the threshold can be determined as qualified waste liquid. For example, 100 waste liquid images are taken in a time period $\Delta T$ when the waste liquid is drained to pass through the transparent pipeline, and each waste liquid image is used for determining the quality of the waste liquid passing through the transparent pipeline through the step 34: a threshold value such as 80 can be set in the step 34, which represents that after at least one selected statistical characteristic value is compared, 80 images in 100 images meet the qualification standard, and the recycled waste liquid is qualified; otherwise, if 80 images in 100 images do not meet the qualification standard, the recycled waste liquid is unqualified.

In some embodiments, determining the quality of the waste liquid can include the following steps: selecting a first statistical criterion from the plurality of statistical criteria to perform waste liquid quality screening on the waste liquid image: and selecting a second statistical criterion from the plurality of statistical criteria to perform waste liquid quality screening on the data left after screening according to the first statistical criterion.

In some embodiments, the operation processing device 24 can further perform quality determination on the waste liquid, includes: selecting a first statistical criterion from the plurality of statistical criteria to perform quality determination on the waste liquid image: selecting a second statistical criterion from the plurality of statistical criteria to perform quality determination on the waste liquid image if the waste liquid image is qualified under the first statistical criterion; and determining that the waste liquid corresponding to the waste liquid image is qualified if the waste liquid image is qualified under the second statistical criterion.

Figure 14:
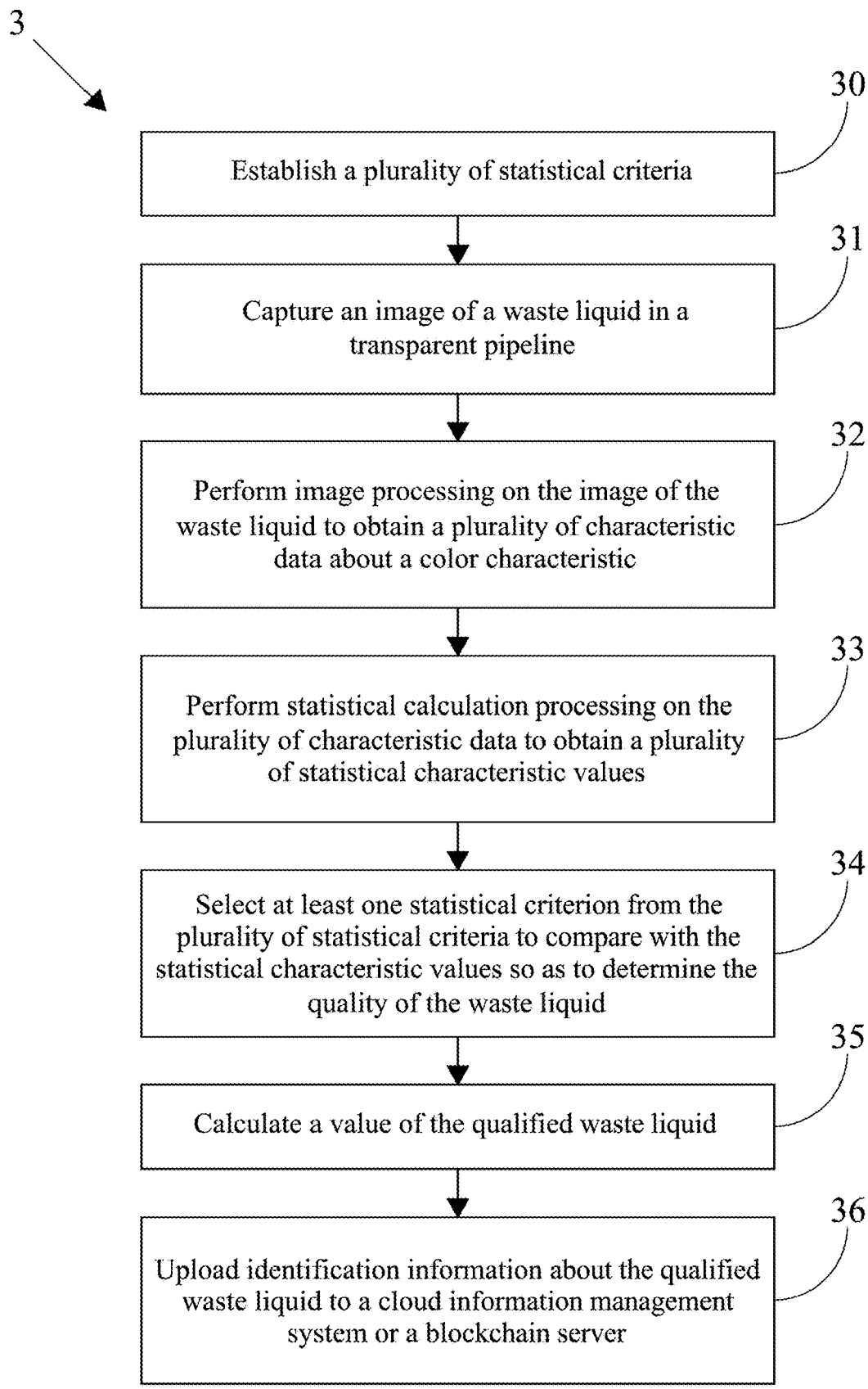
FIG. 14 is a flow schematic diagram of one embodiment of a method for waste liquid recycling with optical inspection of the present disclosure.

FIG. 14 is a flow schematic diagram of one embodiment of a method for waste liquid recycling with optical inspection of the present disclosure. The steps illustrated in FIG. 14 are the same as, or similar to, the steps illustrated in FIG. 1, except that the method of FIG. 14 further includes a step 35 and a step 36. That is, the steps 30-34 in FIG. 14 may be substantially the same as the steps 30-34 in FIG. 1. The step 35 in FIG. 14 may be continued from the step 34 in FIG. 1. In some embodiments, the step 35 may include calculating a value (or price) of the qualified waste liquid through the operation processing device 24 (FIG. 2). In some embodiments, calculating the value (or price) of the qualified waste liquid may include calculating an amount (including but not limited to weight, volume, or flow rate passing through the transparent pipeline) of the qualified waste liquid and estimating the value (or price) of the qualified waste liquid according to the amount and a unit price (e.g., 20 yuan (NEW TAIWAN Dollar, NT$) per kilogram or NT$20 per liter) of the qualified waste liquid. In some embodiments, the value (or price) of the qualified waste liquid may be presented in a manner including, but not limited to, monetary amounts or goods of equivalent value. In some embodiments, the step 35 may further include recycling the qualified waste liquid.

In some embodiments, the step 36 may include uploading identification information corresponding to the qualified waste liquid to a cloud information management system (e.g., 26a of FIG. 2) or a blockchain server (e.g., 26b of FIG. 2). In some embodiments, as shown in FIG. 2, the apparatus 2 for waste liquid recycling may further include a communication unit 25 electrically connected to the operation processing device 24. The apparatus 2 for waste liquid recycling may upload the identification information corresponding to the qualified waste liquid to the cloud information management system 26a or the blockchain server 26b through the communication unit 25. In some embodiments, the identification information may be uploaded to the cloud information management system 26a and the blockchain server 26b simultaneously. In some embodiments, the communication unit 25 may be, for example, a wired communication unit or a wireless communication unit. In some embodiments, the identification information may include, but is not limited to, the compared statistical criterion, the amount of the qualified waste liquid and transaction amount thereof, transaction completion time and place (e.g., address, longitude and latitude information, etc.), and user basic information (e.g., company name, trader's name, phone number, identity information, etc.). In some embodiments, the cloud information management system 26a may receive the uploaded identification information and create corresponding data in a database. The data may be provided to management departments, waste liquid producers/users, or waste liquid recycling companies for query and management in the future. In some embodiments, the identification information uploaded to the blockchain server 26b may further include a cumulative recycling amount of waste liquid (i.e., a sum of multiple recycling amounts of waste liquid) for each apparatus 2 for waste liquid recycling. In some embodiments, the blockchain server 26b may generate at least one equivalent cryptocurrency, form at least one corresponding non-fungible token (NFT), or establish at least one smart contract when the cumulative recycling amount of waste liquid reaches a specific amount (including but not limited to 10,000 kilograms, 10,000 liters, 100,000 kilograms, 100,000 liters, 1,000,000 kilograms or 1,000,000 liters). The NFT is a data unit on the blockchain (digital ledger). Each token can represent unique digital data and serve as an electronic certification or certificate of ownership of virtual goods. Due to its non-fungible nature, the NFT can represent digital assets such as paintings, artwork, sounds, videos, in-game projects, or other forms of creative works (e.g., value or price of the qualified waste liquid). While the works are infinitely replicable, the tokens representing them are fully trackable on their underlying blockchain, providing buyers with proof of ownership. In some embodiments, the cryptocurrency, the NFT, and the smart contract may be traded in a virtual market.

While several embodiments of the present disclosure have been illustrated and described, various modifications and improvements can be made by those skilled in the art. The embodiments of the present disclosure are therefore described in an illustrative but not in a restrictive sense. It is intended that the present disclosure should not be limited to the particular forms as illustrated and that all modifications that maintain the spirit and scope of the present disclosure are within the scope defined in the appended claims.

What is claimed is:

1. A method for waste liquid recycling with optical inspection, comprising:
   establishing a plurality of statistical criteria;
   capturing an image of a waste liquid in a transparent pipeline;
   performing image processing on the image of the waste liquid to obtain a plurality of characteristic data about a color characteristic;
   performing statistical calculation processing on the plurality of characteristic data to obtain a plurality of statistical characteristic values;
   selecting at least one statistical criterion from the plurality of statistical criteria to compare with the statistical characteristic values so as to determine the quality of the waste liquid;
   calculating a value of the qualified waste liquid; and
   uploading identification information corresponding to the qualified waste liquid to a cloud information management system or a blockchain server.

2. The method of claim 1, wherein the identification information includes the compared statistical criterion, the amount of the qualified waste liquid and transaction amount thereof, transaction completion time and place, and user basic information.

3. The method of claim 1, wherein the step of calculating the value of the qualified waste liquid further includes recycling the qualified waste liquid, the identification information includes a cumulative recycling amount of waste liquid, and the blockchain server generates at least one equivalent cryptocurrency according to the cumulative recycling amount of waste liquid.

4. The method of claim 1, wherein the step of calculating the value of the qualified waste liquid further includes recycling the qualified waste liquid, the identification information includes a cumulative recycling amount of waste liquid, and the blockchain server forms at least one corresponding non-fungible token (NFT) according to the cumulative recycling amount of waste liquid.

5. The method of claim 1, wherein the step of calculating the value of the qualified waste liquid further includes recycling the qualified waste liquid, the identification information includes a cumulative recycling amount of waste liquid, and the blockchain server establishes at least one smart contract according to the cumulative recycling amount of waste liquid.

6. The method of claim 1, wherein the color characteristic is selected from the group consisting of red, green, blue, hue, saturation, value, and a combination thereof, and the statistical characteristic value includes mean of saturation (S), mean of hue (H), mean of value (V), mean of red (R), mean of green (G), mean of blue (B), median of saturation (S), median of hue (H), median of value (V), median of red (R), median of green (G), median of blue (B), skewness of saturation (S), skewness of hue (H), skewness of value (V), skewness of red (R), skewness of green (G), skewness of blue (B), standard deviation of saturation (S), standard deviation of hue (H), standard deviation of value (V), standard deviation of red (R), standard deviation of green (G), standard deviation of blue (B), interquartile range of saturation (S), interquartile range of hue (H), interquartile range of value (V), interquartile range of red (R), interquartile range of green (G), interquartile range of blue (B), range of saturation (S), range of hue (H), range of value (V), range of red (R), range of green (G), or range of blue (B).

7. The method of claim 1, wherein establishing the plurality of statistical criteria comprises:
   providing a plurality of waste liquid images;
   performing image processing on the plurality of waste liquid images to obtain a plurality of characteristic data of the color characteristic of each image;
   performing statistical calculation processing on the plurality of characteristic data of each image to obtain a plurality of statistical characteristic values of each image; and
   establishing corresponding statistical criteria according to the statistical characteristic values in the plurality of waste liquid images.

8. The method of claim 1, wherein determining the quality of the waste liquid further comprises:
   selecting a first statistical criterion from the plurality of statistical criteria to perform waste liquid quality screening on the waste liquid image; and selecting a second statistical criterion from the plurality of statistical criteria to perform waste liquid quality screening on the data left after screening according to the first statistical criterion.

9. An apparatus for waste liquid recycling with optical inspection, comprising:
- a transparent pipeline configured to allow a waste liquid to pass through;
- an image capturing device arranged on one side of the transparent pipeline and configured to capture an image of the waste liquid in the transparent pipeline;
- an operation processing device electrically connected to the image capturing device, wherein a plurality of statistical criteria are stored in the operation processing device, and the operation processing device is configured to perform image processing on the image of the waste liquid to obtain a plurality of characteristic data about a color characteristic, perform statistical calculation processing on the plurality of characteristic data to obtain a plurality of statistical characteristic values, select at least one statistical criterion from the plurality of statistical criteria to compare with the statistical characteristic values so as to determine the quality of the waste liquid, and calculate a value of the qualified waste liquid; and
- a communication unit electrically connected to the operation processing device and configured to upload identification information corresponding to the qualified waste liquid to a cloud information management system or a blockchain server.

10. The apparatus of claim 9, wherein the identification information includes the compared statistical criterion, the amount of the qualified waste liquid and transaction amount thereof, transaction completion time and place, and user basic information.

11. The apparatus of claim 9, wherein the identification information includes a cumulative recycling amount of waste liquid, and the blockchain server generates at least one equivalent cryptocurrency according to the cumulative recycling amount of waste liquid.

12. The apparatus of claim 9, wherein the identification information includes a cumulative recycling amount of waste liquid, and the blockchain server forms at least one corresponding non-fungible token (NFT) according to the cumulative recycling amount of waste liquid.

13. The apparatus of claim 9, wherein the identification information includes a cumulative recycling amount of waste liquid, and the blockchain server establishes at least one smart contract according to the cumulative recycling amount of waste liquid.

14. The apparatus of claim 9, wherein the color characteristic is selected from the group consisting of red, green, blue, hue, saturation, value, and a combination thereof; and the statistical characteristic value includes mean of saturation (S), mean of hue (H), mean of value (V), mean of red (R), mean of green (G), mean of blue (B), median of saturation (S), median of hue (H), median of value (V), median of red (R), median of green (G), median of blue (B), skewness of saturation (S), skewness of hue (H), skewness of value (V), skewness of red (R), skewness of green (G), skewness of blue (B), standard deviation of saturation (S), standard deviation of hue (H), standard deviation of value (V), standard deviation of red (R), standard deviation of green (G), standard deviation of blue (B), interquartile range of saturation (S), interquartile range of hue (H), interquartile range of value (V), interquartile range of red (R), interquartile range of green (G), interquartile range of blue (B), range of saturation (S), range of hue (H), range of value (V), range of red (R), range of green (G), or range of blue (B).

15. The apparatus of claim 9, wherein the operation processing device further performs quality determination on the waste liquid, which comprises:
- selecting a first statistical criterion from the plurality of statistical criteria to perform quality determination on the waste liquid image;
- selecting a second statistical criterion from the plurality of statistical criteria to perform quality determination on the waste liquid image if the waste liquid image is qualified under the first statistical criterion; and
- determining that the waste liquid corresponding to the waste liquid image is qualified if the waste liquid image is qualified under the second statistical criterion.

* * * * *